United States Patent [19]
Pastan et al.

[11] Patent Number: 6,156,564
[45] Date of Patent: Dec. 5, 2000

[54] CELLULAR APOPTOSIS SUSCEPTIBILITY PROTEIN (CSP) AND ANTISENSE CSP

[75] Inventors: Ira Pastan, Potomac; Ulrich Brinkmann, Kensington, both of Md.

[73] Assignee: The United States of America as represented by the Department of Health and Human Services, Washington, D.C.

[21] Appl. No.: 08/973,626

[22] PCT Filed: Jun. 7, 1996

[86] PCT No.: PCT/US96/09927

§ 371 Date: Apr. 13, 1998

§ 102(e) Date: Apr. 13, 1998

[87] PCT Pub. No.: WO96/40713

PCT Pub. Date: Dec. 19, 1996

[51] Int. Cl.[7] .................................................. G01N 33/574
[52] U.S. Cl. ........................ 435/287.2; 435/7.1; 435/7.23; 435/810; 530/387.7; 530/387.9; 530/388.85; 530/389.7; 436/501; 436/64
[58] Field of Search ................................ 435/7.1, 7.23, 435/287.2, 810; 530/387.7, 387.9, 388.85, 389.7; 436/501, 64

[56] References Cited

U.S. PATENT DOCUMENTS 5,585,479  12/1996  Hoke et al. .
5,759,782   6/1998  Pastan et al. ................................ 435/6

OTHER PUBLICATIONS

Cohen, J.J., "Apoptis", *Immunol. Today* 14: 126–130, 1993.
Lowe et al., "p53 is required for radiation–induced apoptosis in mouse thymocytes", *Nature* 362:847–849, 1993.
Nathan et al., "Expression of BCL–2 in primary breast cancer and its correlation with tumour pheotype", *Ann. Oncol.* 5:409–414, 1994.
Brinkmann, et al., "Expression Cloning of cDNAs that Render Cancer Cells Resistant to Pseudomonas and Diphtheria Toxin and Immunotoxins", *Molec. Med.* 1: 206–216, 1995.

Xiao, et al., "CSE1 and CSE2, Two New Genes Required for Accurate Mitotic Chromosome Segregation in Saccharomyces cerevisiae", *Mol. Cell. Biol.* 13: 4691–4702, 1993.
Brinkmann, et al., "B3(Fv)–PE38KDEL, a single–chain immunotoxin that causes complete regression of a human carcinoma in mice", Proc. Natl. Acad. Sci. USA 88: 8616–8620, 1991.
Kochi, et al., "DNA Fragmentation and Cytolysis in U937 Cells Treated with Diphtheria Toxin or Other Inhibitors of Protein Synthesis", *Exp. Cell Res.* 208: 296–302, 1993.
Chang, et al., "Internucleosomal DNA Cleavage Precedes Diphtheria Toxin–induced Cytolysis", *J. Biol. Chem.* 264: 15261–15267, 1989.
Morimoto, et al., "Diphtheria Toxin–and Pseudomonas A Toxin–Mediated Apoptosis", *J. Immunol.* 149: 2089–2094, 1992.
Tanner et al., "Increased Copy Number at 20q13 in Breast Cancer: Defining the Critical Region and Exclusion of Candidate Genes", Cancer Res.l 54, 4257–4260, 1994.
Orkin, Stuart H., M.D., et al., "Report and recommendations of the Panel to Assess the NIH Investment in Research on Gene Therapy", Dec. 7, 1995.
Brinkmann et al., "Cloning and characterization of a cellular apoptosis susceptibility gene, the human homologue to the yeast chromosome segregation gene CSE1", Proc. Natl. Acad. Sci. USA 10427–10431 (1995).
Copy of page from International Search Report showing documents considered to be relevant.

*Primary Examiner*—Laurie Scheiner
*Attorney, Agent, or Firm*—Knobbe, Martens, Olson & Bear, LLP

[57] ABSTRACT

The cDNA and amino acid sequences for a cellular apoptosis susceptibility (CAS) protein are used to detect expression and amplification of CAS gene in normal and cancer cells. An antisense CAS gene sequence introduced into living cells inhibits CAS protein activity and thus prevents or inhibits apoptosis in the cells.

14 Claims, 13 Drawing Sheets

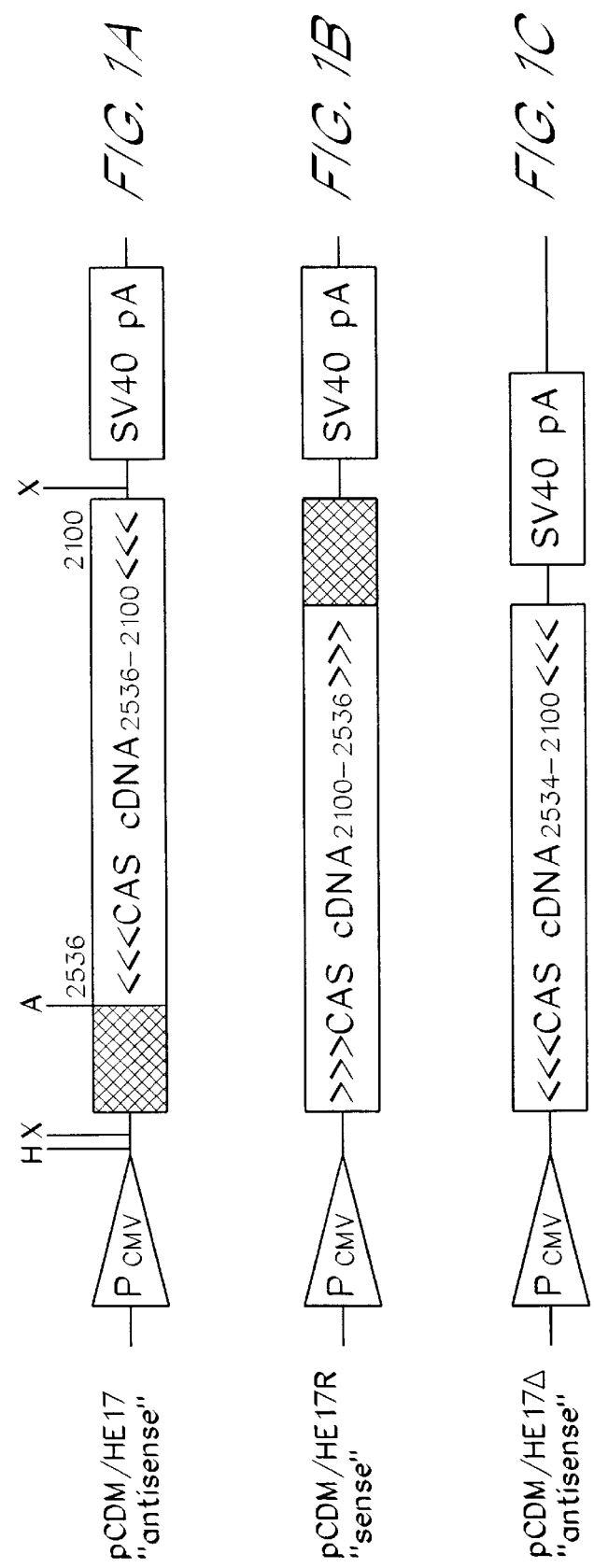

FIG. 6

FIG. 6A. CAS cDNA SEQUENCE

```
GTCGCGCCATTTTGCCGGGGTTTGAATGTGAGGCGGAGCGGCGGCAGGAGCGGATAGTGCCAGCT
ACGGTCCGCGGCTGGGGTTCCCTCCTCCGTTTCTGTATCCCCACGAGATCCTATAGCAATGGAAC
TCAGCGATGCAAATCTGCAAACACTAACAGAATATTTAAAGAAAACACTTGATCCTGATCCTGCC
ATCCGACGTCCAGCTGAGAAATTTCTTGAATCTGTTGAAGGAAATCAGAATTATCCACTGTTGCT
TTTGACATTACTGGAGAAGTCCCAGGATAATGTTATCAAAGTATGTGCTTCAGTAACATTCAAAA
ACTATATTAAAAGGAACTGGAGAATTGTTGAAGATGAACCAAACAAAATTTGTGAAGCCGATCGA
GTGGCCATTAAAGCCAACATAGTGCACTTGATGCTTAGCAGCCCAGAGCAAATTCAGAAGCAGTT
AAGTGATGCAATTAGCATTATTGGCAGAGAAGATTTTCCACAGAAATGGCCTGACTTGCTGACAG
AAATGGTGAATCGCTTTCAGAGTGGAGATTTCCATGTTATTAATGGAGTCCTCCGTACAGCACAT
TCATTATTTAAAAGATACCGTCATGAATTTAAGTCAAACGAGTTATGGACTGAAATTAAGCTTGT
TCTGGATGCCTTTGCTTTGCCTTTGACTAATCTTTTTAAGGCCACTATTGAACTCTGCAGTACCC
ATGCAAATGATGCCTCTGCCCTGAGGATTCTGTTTTCTTCCCTGATCCTGATCTCAAAATTGTTC
TATAGTTTAAACTTTCAGGATCTCCCTGAATTTTGGGAAGGTAATATGGAAACTTGGATGAATAA
TTTCCATACTCTCTTAACATTGGATAATAAGCTTTTACAAACTGATGATGAAGAGGAAGCCGGCT
TATTGGAGCTCTTAAAATCCCAGATTTGTGATAATGCCGCACTCTATGCACAAAAGTACGATGAA
GAATTCCAGCGATACCTGCCTCGTTTTGTTACAGCCATCTGGAATTTACTAGTTACAACGGGTCA
AGAGGTTAAATATGATTTGTTGGTAAGTAATGCAATTCAATTTCTGGCTTCAGTTTGTGAGAGAC
CTCATTATAAGAATCTATTTGAGGACCAGAACACGCTGACAAGTATCTGTGAAAAGGTTATTGTG
CCTAACATGGAATTTAGAGCTGCTGATGAAGAAGCATTTGAAGATAATTCTGAGGAGTACATAAG
GAGAGATTTGGAAGGATCTGATATTGATACTAGACGCAGGGCTGCTTGTGATCTGGTACGAGGAT
TATGCAAGTTTTTGAGGGACCTGTGACAGGAATCTTCTCTGGTTATGTTAATTCCATGCTGCAG
GAATACGCAAAAAATCCATCTGTCAACTGGAAACACAAAGATGCAGCCATCTACCTAGTGACATC
TTTGGCATCAAAAGCCCAAACACAGAAGCATGGAATTACACAAGCAAATGAACTTGTAAACCTAA
CTGAGTTCTTTGTGAATCACATCCTCCCTGATTTAAAATCAGCTAATGTGAATGAATTTCCTGTC
CTTAAAGCTGACGGTATCAAATATATTATGATTTTTAGAAATCAAGTGCCAAAAGAACATCTTTT
AGTCTCGATTCCTCTCTTGATTAATCATCTTCAAGCTGGAAGTATTGTTGTTCATACTTACGCAG
CTCATGCTCTTGAACGGCTCTTTACTATGCGAGGGCCTAACAATGCCACTCTCTTTACAGCTGCA
GAAATCGCACCGTTTGTTGAGATTCTGCTAACAAACCTTTTCAAAGCTCTCACACTTCCTGGCTC
TTCAGAAAATGAATATATTATGAAAGCTATCATGAGAAGTTTTTCTCTCCTACAAGAAGCCATAA
TCCCCTACATCCCTACTCTCATCACTCAGCTTACACAGAAGCTATTAGCTGTTAGTAAGAACCCA
AGCAAACCTCACTTTAATCACTACATGTTTGAAGCAATATGTTTATCCATAAGAATAACTTGCAA
AGCTAACCCTGCTGCTGTTGTAAATTTTGAGGAGGCTTTGTTTTTGGTGTTTACTGAAATCTTAC
AAAATGATGTGCAAGAATTTATTCCATACGTCTTTCAAGTGATGTCTTTGCTTCTGGAAACACAC
AAAAATGACATCCCGTCTTCCTATATGGCCTTATTTCCTCATCTCCTTCAGCCAGTGCTTTGGGA
AAGAACAGGAAATATTCCTGCTCTAGTGAGGCTTCTTCAAGCATTCTTAGAACGCGGTTCAAACA
CAATAGCAAGTGCTGCAGCTGACAAAATTCCTGGGTTACTAGGTGTCTTTCAGAAGCTGATTGCA
TCCAAAGCAAATGACCACCAAGGTTTTTATCTTCTAAACAGTATAATAGAGCACATGCCTCCTGA
ATCAGTTGACCAATATAGGAAACAAATCTTCATTCTGCTATTCCAGAGACTTCAGAATTCCAAAA
CAACCAAGTTTATCAAGAGTTTTTTAGTCTTTATTAATTTGTATTGCATAAAATATGGGGCACTA
GCACTACAAGAAATATTTGATGGTATACAACCAAAAATGTTTGGAATGGTTTTGGAAAAAATTAT
TATTCCTGAAATTCAGAAGGTATCTGGAAATGTAGAGAAAAGATCTGTGCGGTTGGCATAACCA
ACTTACTAACAGAATGTCCCCAATGATGGACACTGAGTATACCAAACTGTGGACTCCATTATTA
CAGTCTTTGATTGGTCTTTTTGAGTTACCCGAAGATGATACCATTCCTGATGAGGAACATTTTAT
TGACATAGAAGATACACCAGGATATCAGACTGCCTTCTCACAGTTGGCATTTGCTGGGAAAAAAG
AGCATGATCCTGTAGGTCAAATGGTGAATAACCCCAAATTCACCTGGCACAGTCACTTCACATG
TTGTCTACCGCCTGTCCAGGAAGGGTTCCATCAATGGTGAGCACCAGCCTGAATGCAGAAGCGCT
CCAGTATCTCCAAGGGTACCTTCAGGCAGCCAGTGTGACACTGCTTTAAACTGCATTTTTCTAAT
GGGCTAAACCCAGATGGTTTCCTAGGAAATCACAGGCTTCTGAGCACAGCTGCATTAAAACAAAG
GAAGTTTTCCTTTTGAACTTGTCACGAAAAAAAAAAAAAAAAAAAAAAAAAAAAAAAAAA
```

FIG. 6B. CAS PROTEIN SEQUENCE

```
MELSDANLQT LTEYLKKTLD PDPAIRRPAE KFLESVEGNQ NYPLLLLTLL EKSQDNVIKV
CASVTFKNYI KRNWRIVEDE PNKICEADRV AIKANIVHLM LSSPEQIQKQ LSDAISIIGR
EDFPQKWPDL LTEMVNRFQS GDFHVINGVL RTAHSLFKRY RHEFKSNELW TEIKLVLDAF
ALPLTNLFKA TIELCSTHAN DASALRILFS SLILISKLFY SLNFQDLPEF WEGNMETWMN
NFHTLLTLDN KLLQTDDEEE AGLLELLKSQ ICDNAALYAQ KYDEEFQRYL PRFVTAIWNL
LVTTGQEVKY DLLVSNAIQF LASVCERPHY KNLFEDQNTL TSICEKVIVP NMEFRAADEE
AFEDNSEEYI RRDLEGSDID TRRRAACDLV RGLCKFFEGP VTGIFSGYVN SMLQEYAKNP
SVNWKHKDAA IYLVTSLASK AQTQKHGITQ ANELVNLTEF FVNHILPDLK SANVNEFPVL
KADGIKYIMI FRNQVPKEHL LVSIPLLINH LQAGSIVVHT YAAHALERLF TMRGPNNATL
FTAAEIAPFV EILLTNLFKA LTLPGSSENE YIMKAIMRSF SLLQEAIIPY IPTLITQLTQ
KLLAVSKNPS KPHFNHYMFE AICLSIRITC KANPAAVVNF EEALFLVFTE ILQNDVQEFI
PYVFQVMSLL LETHKNDIPS SYMALFPHLL QPVLWERTGN IPALVRLLQA FLERGSNTIA
SAAADKIPGL LGVFQKLIAS KANDHQGFYL LNSIIEHMPP ESVDQYRKQI FILLFQRLQN
SKTTKFIKSF LVFINLYCIK YGALALQEIF DGIQPKMFGM VLEKIIIPEI QKVSGNVEKK
ICAVGITNLL TECPPMMDTE YTKLWTPLLQ SLIGLFELPE DDTIPDEEHF IDIEDTPGYQ
TAFSQLAFAG KKEHDPVGQM VNNPKIHLAQ SLHMLSTACP GRVPSMVSTS LNAEALQYLQ
GYLQAASVTL L
```

CELLULAR APOPTOSIS SUSCEPTIBILITY PROTEIN (CSP) AND ANTISENSE CSP

This application is a 371 of PCT/US96/09927, filed Jun. 07, 1996, and a continuation of application Ser. No. 08/480, 662, filed Jun. 07, 1995, now U.S. Pat. No. 5,759,782.

FIELD OF THE INVENTION

The present invention relates to a novel gene sequence coding for a protein which is related to cell proliferation and programmed cellular death (apoptosis), and specifically relates to cDNA and amino acid sequences for this cellular apoptosis susceptibility (CAS) gene and protein.

BACKGROUND OF THE INVENTION

Apoptosis or programmed cell death is a regulated network of biochemical events which lead to cell death. It is a physiological process involved in cell differentiation, organ development and maintenance of cellular population in multicellular organisms (Cohen, J. J., Immunol. Today 14:126–130, 1993). Furthermore, apoptosis is a reaction to various external stimuli and cell damage (e.g. induced by drugs).

Apoptotic cells generally shrink and are phagocytosed by other cells. In contrast, necrotic cells are characterized by swelling, especially of the mitochondria which become dysfunctional, which usually results in cell lysis.

Molecular events characteristics of apoptotic cells include nuclear collapse with condensation of chromatin and loss of nucleoli. Later, the chromatin becomes fragmented into units of single or multiple nucleosomes which present a "ladder" appearance when separated by size on a gel matrix (Compton, M. M., Cancer Metast. Rev. 11:105–119, 1992). Activation of an endogenous endonuclease causes the chromatin fragmentation. Intracellular RNA, especially mRNA, is also degraded early during apoptosis.

Apoptosis can be triggered in various ways, including virus infection, growth factor withdrawal, DNA damage resulting from irradiation, exposure to glucocorticoids and certain chemotherapy drugs, or by signals such as TNF binding to its receptor or crosslinking the Fas receptor with anti-Fas antibodies (Cohen, J. J., Immunol. Today 14:126–130, 1993; Williams, G. T., & Smith, C. A., Cell 74:777–779, 1993; Suda et al., Cell 75:1169–1178, 1993; Smith, et al., Cell 76:959–962, 1994; Lowe et al., Nature 362:847–849, 1993; Sentman et al., Cell 67:879–888, 1991). The mechanism of apoptosis is not well understood, but the observed molecular changes that occur in apoptotic cells suggest that endogenous genes are responsible for apoptosis. The protein produced from these induced genes lead to destruction of RNA and DNA ultimately leading to cell death.

Just as cell death by apoptosis is involved in normal regulation of cellular populations, cell proliferation is also required to maintain homeostasis of tissues and organs. However, in some cells, proliferation is aberrant leading to cancer. Cancer cells can be invasive, metastatic and highly anaplastic.

Although the mechanisms of tumor formation are still not completely and well defined, genetic elements, including oncogenes, have been shown to increase cell proliferation and relieve cells of normal check-points in the cell division cycle. Genes that control cell cycle check points have been identified in multicellular organisms and in yeast where they play an essential role in regulating the cell cycle. It is even possible that cell cycle check points may serve as switch points for choosing between cell proliferation and apoptosis. Thus, when a gene that controls a checkpoint is deleted, mutated, amplified in the genome, or otherwise aberrantly expressed in the cell, it may divert the cell into aberrant proliferation. Similarly, when a gene that normally controls a cell cycle switch point leading to apoptosis is aberrantly expressed, it may result in abnormal cell proliferation.

Some mammalian genes and proteins that have been simultaneously implicated in the regulation of cell proliferation and apoptosis including the genes for p53, BCL-2 or Myc. Although the pathways leading to apoptosis have not been fully elucidated, several genes that play a role in apoptosis have also been shown to play an important role in cancer. The p53 gene, coding for a tumor suppressor, is required for radiation-induced apoptosis (Lowe et al., Nature 362:847–849, 1993). BCL-2 inhibits apoptosis in many cells (Sentman et al., Cell 67:879–888, 1991; Vanhaesebroeck et al., Oncogene 8:1075–1081, 1993) and furthermore, increased BCL-2 gene expression has been detected in primary breast cancer tissue without bci-2 gene amplification (Nathan et al., Ann. Oncol. 5:409–414, 1994).

Apoptosis can also be induced by exposing cells to Diphtheria toxin (DT) or Pseudomonas toxin (PE) (Kochi, S. K., and Collier, R. J., Exp. Cell Res. 208:296–302, 1993; Chang, M. P., et al., J. Biol. Chem. 264:15261–15267, 1989; Morimoto, H., and Bonavida, B., J. Immunol. 149:2089–2094, 1992). Both of these bacterial toxins inhibit eukaryotic protein synthesis by inactivating elongation factor 2 by ADP-ribosylation (Carroll, S. F. and Collier, R. J., J. Biol. Chem. 262:8707–8711, 1987). Although the toxin-specific mechanism by which these toxins induce apoptosis is unknown, it is not simple due to inhibition of protein synthesis because other protein synthesis inhibitors do not induce apoptosis (Chang, M. P., et al., J. Biol. Chem. 264:15261–15267, 1989; Morimoto, H., and Bonavida, B., J. Immunol. 149:2089–2094, 1992).

SUMMARY OF THE INVENTION

According to one aspect of the invention, there is provided a purified and isolated cDNA coding for a human CAS protein having the sequence of SEQ ID NO:1.

According to another aspect of the invention, there is provided a purified and isolated cDNA sequence coding for a portion of human CAS protein consisting of nucleotides 2100 to 2536 of SEQ ID NO:1. In one embodiment, the cDNA sequence is an antisense CAS gene sequence corresponding to nucleotides 2100 to 2536 of SEQ ID NO:1.

According to another aspect of the invention, there is provided a purified and isolated human CAS protein consisting of the amino acid sequence corresponding to amino acids at positions 700–845 of SEQ ID NO:2.

According to another aspect of the invention, there is provided a method of detecting cancerous cells, comprising measuring expression of a human CAS gene at a level higher than expression of a CAS gene in normal noncancerous human cells. In one embodiment of the method, the CAS gene expression is measured by detecting the level of CAS mRNA in cells. The CAS mRNA can be detected by hybridization with a complementary DNA or by a polymerase chain reaction. In another embodiment, CAS gene expression is measured by detecting the level of CAS protein in cells. In a preferred embodiment, the CAS protein is detected by binding of antibody that specifically recognizes CAS protein.

According to another aspect of the invention, there is provided a method of detecting cancer cells, including measuring the number of copies of a CAS gene present in cells, wherein the number of copies of a CAS gene is higher in cancer cells than the number of copies of a CAS gene in normal noncancer cells. In one embodiment of the method, the number of copies of a CAS gene is measured by detecting the amount of hybridization of a DNA complementary to SEQ ID NO: 1 or any portion of 25 or more nucleotides therein. In another embodiment, the method further includes measuring the number of copies of a single-copy gene present in both cancerous and normal noncancerous cells and comparing the number of the single-copy gene to the number of copies of a CAS gene, wherein the number of copies of the CAS gene is higher than the number of copies of the single-copy gene. In one embodiment of the method, the number of copies of a CAS gene is determined by a polymerase chain reaction that amplifies either a 5' portion of the CAS gene, a 3' portion of the CAS gene, or both 5' and 3' portions of the CAS gene. In preferred embodiments of the method, the cancer cells are from breast, colon or lymph tissue. In one embodiment there is provided a kit for utilizing the method of this aspect of the invention, wherein the kit includes polynucleotides that serve as primers in a polymerase chain reaction for direct amplification of a nucleic acid coding for CAS protein and one or more reagents for performing a polymerase chain reaction or detecting a product of the polymerase chain reaction.

According to another aspect of the invention, there is provided a purified and isolated antibody that specifically recognizes CAS protein. One embodiment is a kit that utilizes the antibody for diagnosing cancer, including an antibody that specifically recognizes CAS protein and a means for indicating binding of the antibody to CAS protein.

According to another aspect of the invention, there is provided a method for preventing or reversing apoptosis in a mammalian cell, including the steps of providing the CAS cDNA sequence of SEQ ID NO:1 in a vector such that an antisense CAS transcript will be made in a cell under the regulation of DNA sequences contained within said vector, and administering an effective amount of the vector containing SEQ ID NO:1 to a mammalian cell thereby delivering the vector and CAS cDNA intracellulary.

cancer in a mammal in need of treatment, including administering to the mammal an agent that decreases CAS protein activity in cells, wherein the agent is an antibody that specifically recognizes CAS protein or an antisense CAS gene sequence that inhibits CAS protein activity by decreasing expression of a CAS gene. In a preferred embodiment, the agent is an antisense CAS gene sequence of the sequence of nucleotides 2100 to 2536 of SEQ ID NO:1 in a vector that includes genetic elements that regulate transcription of the antisense CAS gene sequence.

The foregoing general description and the following detailed description, with the accompanying drawings and examples, explain the principles of the invention and illustrate various embodiments of the invention.

BRIEF DESCRIPTION OF THE DRAWINGS

FIG. 1 is a diagram of three plasmids showing the CAS cDNA clones in the "antisense" (FIG. 1A, pCDM/HE17) and "sense" (FIG. 1B, pCDM/HE17R) directions containing unrelated DNA (shadowed), and in the "antisense" direction (FIG. 1C, pCDM/HE17Δ) without the unrelated DNA.

FIG. 6 shows the DNA sequence of the CAS cDNA (FIG. 6A, SEQ ID NO:1) and the corresponding amino acid sequence (FIG. 6B; SEQ ID NO:2).

DETAILED DESCRIPTION OF THE INVENTION

Figure 2A:
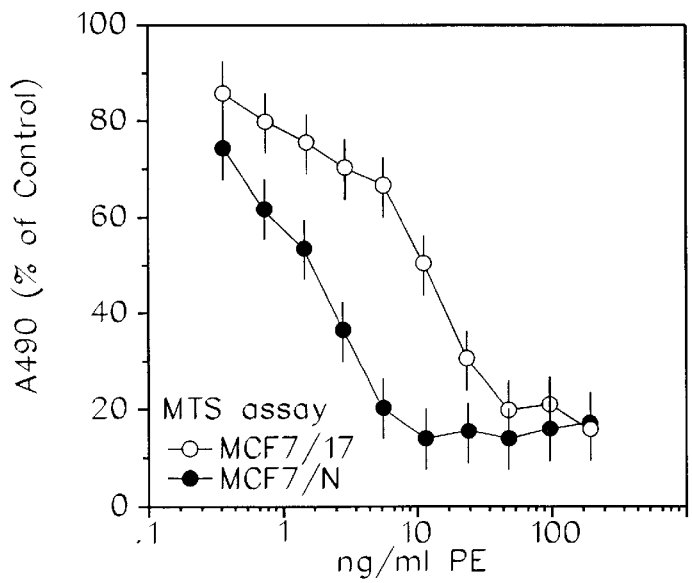
FIG. 2 shows that CAS antisense reduces the sensitivity of MCF-7 cells to PE as determined by the MTS assay (FIG. 2A and 2B), even though protein synthesis is inhibited (FIG. 2C), and by time course experiments in which antisense tranfectants undergo growth arrest upon toxin treatment but recover after removal of toxin (FIG. 2D–2F).

*Diphtheria* toxin (DT) and *Pseudomonas* toxin (PE) are toxins that affect ADP-ribosylation that have been used to make recombinant immunotoxins that can specifically target and kill cancer cells in vitro and in vivo (Brinkmann, U., et al., *Proc. Natl. Acad. Sci. USA* 88:8616–8620, 1991; Pastan I., et at.,*Annu Rev. Biochem.* 61:331–354, 1992; Brinkmann U., and Pastan I., *Biochem Biophys. Acta.* 1198:27–45, 1994). However, it is known that for other anti-cancer agents, treated cells can become drug resistant causing the drugs to loose their efficacy (Schimka, R. T., *Cell* 37:705–713, 1988; Gottesman, M. M., and Pastan, I., *Annu. Rev. Biochem.* 62:385–427, 1993). Several known mechanisms by which cells can become resistant to ADP-ribosylating toxins, and thus possibly also to anti-cancer immunotoxins, include altered toxin binding, internalization, processing, and alterations in elongation factor 2 (EF2), the intracellular toxin target (Laurie and Robbins, 1991; Kido et al., 1991; Fendrick et al., 1992; Chaudhary et al., 1990).

We have used expression cloning to isolate cDNA-containing plasmids that cause breast cancer cells (e.g., cell line MCF-7) to become immunotoxin-resistant (Brinkmann, U., et al., *Molec. Med.* 1:206–216, 1995). Using this approach, we isolated a gene that renders cells resistant to PE and DT. Because PE and DT induce apoptosis, the resistance of cells containing these clones suggested that the cloned cDNA was related to regulation of apoptosis. Hence we named the gene "CAS" for Cellular Apoptosis Susceptibility, in reference to the function of the protein product of the gene. Plasmids containing even a portion of the CAS gene rendered the MCF-7 cells resistance to native PE and DT, indicating that the resistance was due to interference with the action of the toxin moiety rather than another portion of the immunotoxins.

In cells transfected with the CAS clones, the cells did not die upon exposure to PE or DT, even though the toxins caused modification of EF2 and inhibition of protein synthesis comparable to toxin-sensitive control sells. Thus, these clones represent a class of genes that determine the sensitivity of cells to toxin after inhibition of protein synthesis, the primary action of the toxins, has occurred. The isolated and purified cDNA coding for the CAS protein is the subject of this invention.

The clone that mediated PE- and DT-resistance of transfected MCF-7 cells, without interfering with ADP-ribosylation of EF2 and subsequent inhibition of protein synthesis, contains an antisense CAS cDNA fragment. MCF-7 cells containing the antisense CAS cDNA clone were less susceptible to toxin induced apoptosis and apoptosis induced by TNF-alpha and TNF-beta. These results show that the gene has a function in apoptosis. Independent from that function in apoptosis, we found that expression of the human CAS gene was elevated in tissues containing many dividing cells and in tumor cell lines, indicating that CAS also has a role in cell proliferation. The CAS gene sequence is partially homologous with that of the yeast CSE1 gene, which plays a role in yeast cell division (Xian, Z., et al., *Mol. Cell. Biol.* 13:4691–4702, 1993).

The present invention includes a complete cDNA sequence coding for CAS protein and the corresponding complete amino acid sequence of CAS protein. The sequences are useful for making purified CAS protein which can be used to develop protein-based kits for detection of CAS protein, a potential marker for cancer, in human cells and tissue. The DNA sequence, in whole or part, can be used as a probe to detect gene expression and genetic rearrangements of the CAS gene and the surrounding chromosomal region. This is useful for diagnosing cancer and determining its degree of malignancy based on CAS gene expression or genetic rearrangement. This aspect is especially important in diagnosing and treating cancer by indicating the physiological condition of cancerous cells thus allowing a clinician to administer an appropriate treatment for the detected cancer. The sequence may be useful as an antisense therapeutic composition for decreasing functional CAS expression intracellularly and thus controlling growth of malignant cells or tissue. The sequence may also allow one to induce abnormal physiological conditions in a mammal by overexpressing the CAS gene to create animal models for human pathological conditions (e.g., breast and colon cancer) which are useful for discovery of new therapeutics to improve the current treatments of these conditions.

A clone containing a CAS cDNA was isolated from a cDNA library utilizing a selection for immunotoxin resistance in cells transfected with the CAS cDNA clone. That is, an immunotoxin in which a truncated form of the toxin PE is joined to the variable region of an antibody that recognizes cellular marker molecule is used to select stably transfected cells that survive incubation with the immunotoxin. The immunotoxin kits cells by delivering a toxin that causes cell death by inactivating EF2 by ADP-ribosylation of the elongation factor, thereby arresting protein synthesis in the cells. Clones from a library of human cDNA molecules that are expressed from a promoter and other translational signals were stably transfected into immunotoxin-sensitive recipient cells using any of a variety of transfection methods including electroporation. Cotransfection of additional plasmids to provide other selectable drug resistance markers or expression signals for transcription and/or translation of the transfected human cDNA may also be used. The recombinant cell lines were then selected for their immunotoxin resistance, either as stable clones or as transiently expressing clones.

Using this approach, a transfected cell line containing a clone that made the transfected cells about ten-fold less sensitive to the PE-derived immunotoxin was isolated. The cells were also demonstrated to be resistant to native PE and DT, but were not resistant to ricin or cycloheximide, drugs that inhibit protein synthesis by other mechanisms. The clone that conferred this PE and DT resistance contained a cDNA that was transcribed to produce an antisense RNA molecule. The sequence of the cDNA was determined using standard DNA sequencing procedures and revealed a cDNA fragment of a previously unidentified human homolog of the yeast gene CSE1, a chromosome segregation gene. The human gene was designated CAS for "cellular apoptosis susceptibility" because subsequent experiments showed that the gene was involved in the process of apoptosis. Unrelated sequence contained in the cDNA clone was also revealed by DNA sequencing buy was a cloning artifact because the unrelated sequence was not found associated with a full length CAS clone subsequently isolated and did not contain an open reading frame nor was it expressed in the RNA of any human tissue tested by Northern blotting.

The antisense CAS cDNA was responsible for conferring toxin resistance to the transfected cells because a subclone containing the CAS cDNA in an orientation that produces sense RNA did not render the cells toxin resistant. The PE-resistance of cells containing CAS cDNA in an orientation that produces antisense CAS RNA was confirmed in assays measuring cell proliferation over multiple days. In those assays, the cells containing antisense CAS constructs demonstrated growth arrest upon toxin treatment but maintained cell viability and recovered showing cell proliferation when the toxin was removed, reaching about the same cell number as the control cells that were not PE treated after a few days of resumed growth. In contrast, control cells treated with PE died as a consequence of toxin treatment. The viability of cells containing antisense CAS was confirmed by morphological observations in which the CAS antisense containing cells maintained a viable appearance (flattened and attached to the substrate) during PE treatment whereas control cells detached from the substrate and began to disintegrate.

Cells containing antisense CAS cDNA constructs, like control cells, have protein synthesis inhibited by inactivation of EF2 as demonstrated by an assay that measures incorporation of radioactivity into protein. The PE-mediated alteration of EF2 was directly confirmed in an ADP-ribosylation assay. Thus, the CAS antisense did not make cellular EF2 resistant to PE but mediated cellular resistance to the toxin by another mechanism. This is related to CAS protein production in the transfected cells because the antisense CAS constructs reduced the level of CAS protein about 65% compared to controls, as detected by immunoblotting assays in which anti-CAS polyclonal antibodies specifically detected CAS protein of about 100 kDa.

Nuclear DNA degradation associated with toxin-induced apoptosis was decreased in cells containing antisense CAS constructs. The nuclear DNA degradation resulting from PE treatment of control cells that did not have antisense CAS released DNA fragments into the culture medium and produced DNA with a characteristic "ladder" appearance (resulting from internucleosomal DNA degradation) when visualized on a gel. In contrast, antisense CAS containing cells treated with PE showed considerably less soluble DNA in the medium and showed only a very faint "ladder" pattern with most of the DNA remaining in high molecular weight form of greater than 1500 bp. These results suggest that CAS antisense produces toxin resistance by interfering with the apoptosis pathway. Hence, the presence of CAS protein makes cells susceptible to apoptosis.

Because apoptosis is known to be induced in cells exposed to tumor necrosis factors (TNF) α and β, the effect of CAS antisense was determined in transfected cells containing CAS antisense was determined in transfected cells containing CAS antisense constructs. All of the cells tested were shown to have TNF receptors using binding assays to detect binding of radiolabeled TNF-α. Control cells were about 5-fold to 10 fold more sensitive to both TNF-α and TNF-β than cells containing antisense CAS as determined by an assay to measure radioactivity incorporation into proteins. This CAS antisense mediated resistance to TNF-α and TNF-β was confirmed by morphological observation of the treated cells, which remained normal compared to the killed control cells. Cell proliferation assays also confirmed that CAS antisense transfected cells were growth inhibited by TNF treatment but the inhibition was reversed when TNF was removed.

Using the cDNA clone containing 436 bp of CAS cDNA as a probe, longer clones containing up to 2.4 kb of CAS cDNA were isolated from a human cDNA library; these clones all contained 3' end CAS cDNA. A full length CAS cDNA clone was expected to be about 3.2 kb long based on the size of CAS mRNA detected in Northern blots of RNA obtained from human cell lines. To isolate a full length CAS cDNA clone, polymerase chain reaction amplification of the 5' portion of the CAS cDNA clone. From these clones, the complete CAS cDNA sequence was determined (SEQ ID NO:2) and the amino acid sequence of the CAS protein was deduced (SEQ ID NO:2). When the coding regions of the human CAS gene and the yeast CSE1 gene were compared, their sequences were about 59% homologous overall and a search of DNA and protein databases revealed no ohter defined protein with significant homology to CAS (Brinkmann, U. et al., Proc. Natl. Acad. Sci. USA 92:10427–10431, 1995).

CAS gene expression in a variety of normal human tissues and human cancer cell lines was demonstrated using Northern blotting. The CAS mRNA (about 3 kb in length), was found in RNA from pancreas, adrenal medulla, thyroid, adrenal cortex, testis, thymus, small intestine, stomach, spleen, lymph node, thymus, appendix, peripheral blood, bone marrow, fetal liver, spleen, prostate, ovary, colon, heart, brain, placenta, lung, liver, skeletal muscle and kidney tissues, as well as tumor cell line RNA from a variety of cell lines. Quantitation of CAS expression, normalized to the expression of actin or GAPDH, showed that relative expression of CAS was high in tissue containing many actively proliferating cells (e.g., testis and fetal liver), and was elevated above basal level in tissues that contain come proliferating cells (e.g., lymphoid tissues). Thus, in addition to its role in apoptosis, CAS expression is associated with cell proliferation.

Anti-CAS polyclonal antibodies were produced in animals immunized with purified recombinant CAS proteins containing amino acids 1–284 and 327–669 of the complete CAS amino acid sequence. The anti-CAS specific antibodies were purified using standard techniques and used to detect CAS protein on immunoblots of gel separated cellular proteins, detecting a single band of about 100 kDa. The anti-CAS antibodies have been used to determine the relative expression of CAS protein in resting (normal) cells compared to proliferating and tumor cells, and to determine the cellular location of CAS protein.

Because CAS mRNA is highly expressed in proliferating cells and tumor cell line, proteins in cell extracts made from growth arrested and actively growing human cells were analyzed for production of CAS protein. Growth arrested cells that were serum starved produced considerably less CAS protein than actively growing cells indicating that elevated CAS protein is a marker for cell proliferation. When proteins extracted from breast cancer cells were compared to normal (fibroblast) cell proteins, elevated levels of CAS protein were detected by immunoblotting showing that CAS is expressed in significantly higher levels in cancer cells, thus indicating that anti-CAS antibodies are useful for diagnosing cancer by detecting elevated CAS levels in cancer cells. Such an anti-CAS antibody based diagnostic kit may utilize any of a variety of known immunoassays including but not limited to fluorescently-labelled antibody detection, radioimmunoassay (RIA), colorimetric antibody detection such as using antibody linked to latex beads or an enzyme linked immunosorbent assay (ELISA), and a sandwich immunoassay involving multiple reagents.

The cellular location of CAS protein was also determined using anti-CAS antibodies in immunoblotting analyses. The CAS protein is a relatively abundant protein (about 600,000 molecules per cell) found in the cytosol. Using immunofluorescent labeling of cellular substructure, the CAS protein was associated with microtubules, similar to the location of the protein tubulin, and in mitotic cells CAS is associated with the mitotic spindle (Scherf, U. et al. Proc. Natl. Acad. Sci. USA 93:2670–2674, 1996). These immunofluorescent labeling results confirmed that CAS is present in elevated amounts in proliferating cells including testicular spermatogonia, basal cells of the colon, and in the respiratory epithelium of the trachea and in axons and Purkinje cells of the cerebellum. Using anti-CAS antibodies in immunostaining analysis of formalin-fixed tissues, these results were extended to lymphoid tissue found in normal tonsil-tissue and lymphomas. CAS protein was detected in tonsil tissue, primarily in cytoplasm of large cells of the dark zone of the follicle but not in mantle zone cells or interfollicular cells. In many different types of lymphomas, CAS protein was also found in many cells, generally correlating with the distribution of another cellular proliferation protein marker (Ki-67), and found predominantly in the larger malignant cells of the tumors, thus showing that CAS is useful as a marker for cancer cells.

Utilizing Southern blotting techniques with a CAS genetic probe and fluorescent in situ hybridization with a CAS-containing P1 clone, the CAS gene was localized to human chromosome 20 in the 20q13 region, a region that is known to be amplified in some breast cancers, colon and bladder cancer cell lines (Brinkmann, U. et al., Genome Res. 6:187–194, 1996). Quantitative Southern blotting was used to determine that the CAS gene was amplified (two- to eight-fold) compared to a single-copy gene (e.g., actin) in a number of cancer cells lines, particularly in breast cancer, colon cancer and leukemia lines. More detailed information on the genetic amplification of the CAS gene was obtained using Fluorescent In Situ Hybridization (FISH), comparing CAS in cancer cell lines to the CAS gene detected in normal human peripheral blood lymphocytes (PBL) which have two copies of the CAS gene and 46 chromosomes per cell. Many of the tested breast and colon cancer cell lines and one leukemia showed amplification of the CAS gene associated with some chromosomal abnormalities, such as an extra copy of chromosome 20, an aberrant chromosome 20 such as no normal chromosome 20 but detection of 20q marker chromosomes, an amplification of the 20q region, or a CAS-specific amplification and translocation to another chromosomal region than 20q. Other chromosomal abnormalities (e.g., polyploidy) were also detected in the cancer cell lines. Thus, the CAS gene serves as a useful marker of chromosomal abnormalities in chromosome 20, particularly in the 20q region, associated with breast and colon cancers and leukemia.

A complete genomic clone of the CAS gene was isolated from a human genomic library and the presence of the 5' and 3' ends of the CAS gene on the clone were confirmed using PCR amplification of the ends of the CAS gene, using primers based on the sequence of the CAS cDNA at the 5' and 3' ends. A similar PCR-based assay using primers specific for the CAS gene sequence is useful for detecting amplification of CAS gene sequences in DNA isolated from human tissue as the template. In this PCR-based assay, genomic DNA is isolated from tissue to be tested (e.g., a biopsy of breast tissue) and the DNA is used as a template for a PCR amplification of either 5' end, a 3' end or both 5' and 3' ends of the CAS gene using appropriate combinations of primers specific for amplifying the respective end(s) of the CAS gene. The PCR amplification of the CAS gene is compared to a PCR amplification of a known single-copy gene in human DNA (e.g., actin). Using appropriate calculations to normalize the amount of amplification of the portion of single-copy gene compared to the amplified portions(s) of the CAS gene (i.e., based on the relative sizes of the amplified gene portions), the number of copies of the CAS gene in the tissue is approximated to serve as a diagnostic for cancer tissue and as a prognosticator of the aggressiveness of the cancer if cancer is detected. For example, about a two-fold amplification of the CAS gene relative to the control single-copy gene in the tissue DNA indicates that there is probably a 20q chromosomal abnormality in the tissue DNA, indicative of cancer. Additional amplification of the CAS gene detected in the tissue DNA (e.g., greater that two-fold) in an indicator of an aggressive cancer which is used by the treating physician in making a prognosis and deciding on appropriate therapy.

The general principles of the present invention may be more fully appreciated by reference to the following examples.

EXAMPLE 1

ISOLATION OF A cDNA CLONE THAT RENDERS A BREAST CANCER CELL LINE RESISTANT TO CELL DEATH INDUCED BY TOXINS

Expressing cloning and immunotoxin selection of cDNA plasmids.

A cDNA library in plasmid pCDM8 that contains HeLa cDNA expressed from a CMV promoter and followed by a SV40 polyA sequence was obtained from Clontech and transfected into MCF-7 breast carcinoma cells. Clones of human cDNAs that confer resistance to the immunotoxin B3(Fv)-PE38KDEL were isolated by expression cloning and selection (Brinkmann, U., et al., *Molec. Med.* 1:206–216, 1995) with the immunotoxin B3(Fv)-PE38KDEL, a fusion protein composed of a truncated form of PE and the Fv region of monoclonal antibody (MAb) B3 that binds to a carbohydrate present on many carcinomas and cancer cell lines, including MCF-7 cells, and kills them (Brinkmann, U., et al., *Proc. Natl. Acad. Sci. USA* 88:8616–8620, 1991).

Briefly, MCF-7 cells expressing the SV40 T antigen, which allows episomal replication in the cells, (MCF-7/T; Brinkmann, U., et al., *Mole. Med.* 1:206–216, 1995) were transfected with a HeLa cDNA expression library and treated two days later with high dose of B3(Fv)-PE38KDEL (Brinkmann, U., et al., *Proc. Natl. Acad. Sci. USA* 88:8616–8620, 1991). Dead cells were removed by washing with phosphate buffered saline (PBS), the remaining cells harvested, and plasmids wre recovered (Hirt, B., *J. Mol. Biol.* 26:365–369, 1967). The recovered plasmids were propagated and amplified in *E. coli* (strain MC1061/P3) using 35–50 µg/ml ampicillin and 12.5–15 µgl/ml tetracycline. Plasmid DNA for transfections was purified by standard techniques well known in the art based on elution from DEAE-Sephacel (using a Qiagen™ "Mega" plasmid DNA preparation kit) and retransfected into MCF-7/t for two additional rounds of immunotoxin-selection and plasmid reisolation as described above. Using this procedure, plasmids that caused cells to survive after immunotoxin exposure were selectively enriched resulting in siblings of the same or overlapping cDNAs in the final plasmid pool analyzed. Such plasmids were identified by DNA hybridization analysis and several plasmids were found that were present more than once in a pool of 96 individual plasmid clones randomly isolated after three rounds of immunotoxin selection.

These toxin-resistance clone candidates were stably transfected into MCF-7 cells and analyzed individually for their effects on toxin sensitivity (as described in Brinkmann, U., et al., *Molec. Med.* 1:206–216, 1995). Cell line MCF-7/17 that contains a plasmid, pCDM/HE17, called "p17" in Brinkmann, U., et al., *Molec. Med.* 1:206–216, 1995) was obtained by cotransfection with another plasmid, pMC1neo/polyA, that confers resistance to the drug G418 which was used to select transformants using standard tissue culture methods.

Molecular manipulations of clones.

pCDM/HE17 was isolated from that library by immunotoxin selection and contains a 700 bp insert composed of 436 bp of antisense cDNA called CAS and 264 bp of unrelated sequence (FIG. 1). The CAS gene was identified as an open reading frame with homology to a yeast gene, CSE1 (Xiao, Z., et al., *Mol. Cell. Biol.* 13:4691–4702, 1993). Standard cloning techniques (Sambrook, J., et al., *Molecular cloning. A Laboratory Manual.*, 2nd ed., 1989) were used to make pCDM8/HE17R, a plasmid containing the 700 bp cDNA in an inverse orientation, and pCDM8/HE17Δ, a plasmid in which a 260 bp Asp700-HindIII fragment that is not homologous to a CSE1 sequence has been deleted.

The relevant portions of these three plasmids are diagrammed in FIG. 1. Plasmid pCDM/HE17 contains a 700 bp insert composed of 436 bp antisense cDNA (open box), which is homologous to the yeast CSE1 gene, and 264 bp unrelated sequence (shadowed box) in an antisense direction behind the CMV promoter followed by the SV40 poly-A signal. X,A and H indicate Xbal, Asp700 and HindIII sites. pCDM/HE17 contains the cDNA (Xbal-fragment) of pCDM/HE17 in reverse orientation and pCDM8/HE17Δ has the 260 bp Asp700-HindIII non-CSE1 fragment deleted. As negative controls, four plasmids containing unknown inserts (pCDM8/C2-pCDM8/C5) were randomly chosen from the same library.

Recombinant MCF-7 cell lines.

Cell lines were produced by electoporation of 5×10$^8$ MCF-7 cells with 3 µg pMC1neo/polyA and 15 µg of expression plasmid, using a Biorad™ gene pulser at 400 V, 960 FD, in 0.4 cm cuvettes (as described in Brinkmann, U., et al., *Molec. Med.* 1:206–216, 1995). MCF-7/T cells are a pool of MCF-7 cells that express SV40 large T antigen, thus allowing episomal replication of plasmids with an SV40 origin (e.g., pCDM8). MCF-7/T cells were made by cotransfection of pCMV-TAg (Ogryzko, V. V., et al., *J. Virol.* 68:3724–3732, 1994) and pMC1neo/polyA and selection of a transfected cell pool with 0.8 mg/ml G418 (FIG. 1A). Similarly, MCF-7/17, MCF-7/17R and MCF-7/17Δ cell pools were produced by cotransfection of pMC1neo/polyA and 15 μg of pCDM/HE17, pCDM/HE17R or pCDM/HE17Δ, respectively. MCF-7/C and MCF-7/C2–C5 cells were produced by cotransfection of pMC1neo/polA with pCDM8 (vector alone, to produce MCF-7/C cells) or pCDM/C2–C5 (to produce MCF-7/C2–C5 cells), control plasmids randomly chosen from the library without any selection. MCF-7/N cells contained only pMC1neo/polyA. All these cell lines were selected and propagated with media containing 0.8 mg/ml G418 and were not exposed to toxins or TNF until their response to these agents was tested.

One clone that conveyed immunotoxin resistance on MCF-7 breast cancer cells is pCDM/HE17, a plasmid containing a 700 bp HeLa cDNA insert (FIG. 1). This clone rendered MCF-7 cells about 10-fold less sensitive to a PE-derived immunotoxin as well as to native PE and DT (Brinkmann, U., el al., *Molec. Med. 1:206–216, 1995*). Both toxins usually cause cell death by inactivating EF2 (by ADP-ribosylation of the protein), thereby arresting protein synthesis. Although cells containing clone pCDM/HE17 were resistant to PE and DT (about 10-fold compared to control MCF-7/N cells, they were not resistant to ricin or cycloheximide (having a $LC_{50}$ of about 250 ng/ml), which inhibit protein synthesis by other mechanisms (Brinkmann, U., et al., *Molec. Med.* 1:206–216, 1995), nor are they protected against cell death induced by various chemotherapeutic agents, e.g., VP 16 (having a $LC_{50}$ of 30 μg/ml) and staurosporine (having a $LC_{50}$ of 1–2 ng/ml).

The cDNA insert in plasmid pCDM/HE17 was determined using fluorescently labeled dideoxynucleotides essentially according to the method of Sanger et al. (*Proc. Natl. Acad. Sci. USA* 74:5463, 1977) using an automated sequencer (ABI™ model 373A and the ABI™ Dyedeoxy Terminator kit).

The DNA sequence of pCDM/HE17 cDNA revealed a 436 bp cDNA fragment that is part of a previously unidentified human homolog of the yeast CSE1 chromosome segregation gene (Xiao, Z., et al., *Mol. Cell. Biol.* 13:4691–4702, 1993), which we call CAS. The human CAS cDNA clone has 45% protein identity and 66% similarity of amino acids when compared to the yeast CSE1 sequences (Xiao, Z., et al., *Mol. Cell. Biol.* 13:4691–4702, 1993) in this portion of the DNA (discussed in detail in Example 9). Plasmid pCDM8/HE17 also contains 264 bp of an unrelated sequence fused to CAS sequences. This is library-ligation artiface because this sequence is not related to the sequence of the full length CAS isolated from human placenta cDNA (discussed in Example 7) and also not linked to the gene in HeLa cells, as shown by hybridization of Southern blots of HeLa and placenta DNA cleaved with various enzymes. This unrelated sequence does not have any open reading frame and therefore is noncoding, and its expression was not detected by Northern blot analysis of RNA from any human tissue. The CAS clone is present in an "inverse" orientation so that transcription from the CMV promoter of pCDM/HE17 generates an antisense RNA. Therefore, the resistance mediated by pCDM/HE17 is likely due to antisense RNA produced from this partial CAS gene sequence which interfers with expression of the human CAS gene.

EXAMPLE 2

CELLULAR RESISTANCE TO TOXINS IS MEDIATED BY CAS ANTISENSE RNA

To confirm that toxin resistance mediated by clone pCDM/HE17 is caused by antisense RNA production of CAS RNA, a plasmid (called pCDM/HE17R; see FIG. 1B) was constructed in which the insert of pCDM/HE17 was inverted so that sense RNA fragment would be made from the plasmid. This plasmid did not render cells resistant. To rule out a possible effect of the additional non-CAS sequence, the 264 bp sequence that showed no homology to the yeast CSE1 gene was also deleted, to produce plasmid pCDM/HE17Δ (FIG. 1). These plasmids were individually cotransfected with plasmid pMC1neo/polyA into MCF-7 cells and stably transfected cells containing pMC1neo/polyA and each of these plasmids were isolated. Additional controls were MCF-7 cells with randomly chosen plasmids from the unselected pCDM8/HeLa library (called MCF-7/C2–C5), and MCF-7 cells with pMC1neo/polyA alone (called MCF-7/N). Cells were propagated using G418-resistant drug selection. Cells were not exposed to toxin until their response to toxins was analyzed. All transfectants (including the parent clone, MCF-7/17) were pooled transfectants (greater than 10 colonies) rather than isolated single clones to compensate for possible clonal variability in the cells containing the transfected plasmids (Brinkmann, U., et al., *Molec. Med.* 1:206–216, 1995).

FIG. 2 shows experiments in which the sensitivity to PE of MCF-7 cells and CAS antisense transfected MCF-7 cells was analyzed using the MTS cell proliferation assay. PE was chosen to represent ADP-ribosylating toxins (which also include immunotoxins and DT) in this study because the relative sensitivities or resistance of the cell lines to PE, DT and immunotoxins were comparable, i.e., cells resistant to PE also were resistant to immunotoxin as well as to DT (Brinkmann, U., et al. *Molec. Med.* 1:206–216, 1995).

Sensitivity to PE was assayed by MTS assays (Cory, A. H., et al. *Cancer Commun.* 3:207–212, 1991) which detect dehydrogenases present in living cells (using absorbance at 490 nm which is proportional to number of live cells), or by assaying incorporation of $^3$H-leucine into cellular proteins (protein synthesis inhibition assay; Brinkmann, U., et al., *Proc. Natl. Acad. Sci. USA* 88:8616–8620, 1991). Usually $3 \times 10^3$ cells/well in 200 μl medium were plated and grown overnight, incubated with toxin for 20 hrs (or as indicated), and then assayed. Referring to FIG. 2, the symbols are the same for all experiments. MCF-7/17 cells (○) and MCF-7/17Δcells (Δ) contained CAS antisense clones. Controls were MCF-7/N cells (●) which contained only the pMC1neo/polyA plasmid and MCF-7/C cells (■) which contained pMC1neo/polyA and the pCDM8 library vector without insert. The MCF-7/17R cells (▲) contained CAS cDNA in the sense direction (see FIG. 1 for diagrams of the plasmids with CAS inserts).

FIG. 2A shows an experiment in which cells were exposed to various concentrations of PE for 3 days and the number of cells present on day 3 was measured by MTS assay. It is evident that MCF-7/17 cells containing CAS antisense were about 10-fold more resistant to PE than the control cell lines (MCF-7/N) and MCF/C, with an $IC_{50}$ of about 15 ng/ml compared to 1–2 ng/ml in the control. To eliminate the possibility that the additional non-CAS sequence influences toxin sensitivity, MCF-7/17Δ cells containing CAS antisense without the additional sequence were also tested.

Figure 2B:
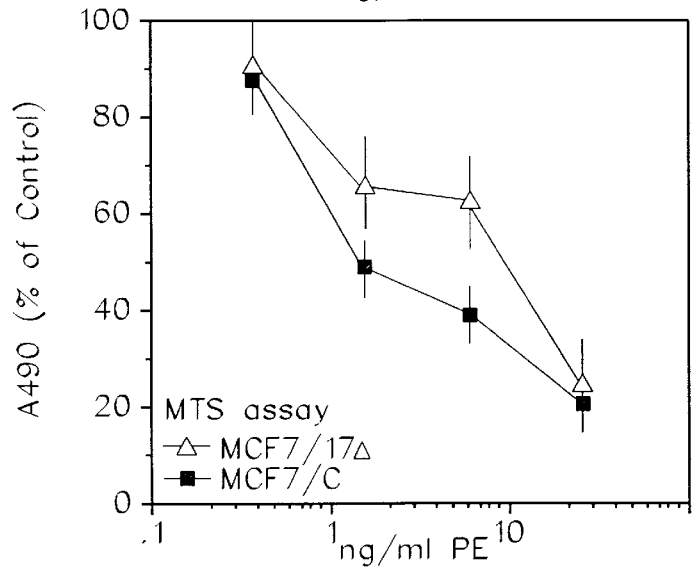

FIG. 2B shows that these cells were also more resistant to PE, although the resistance was not as pronounced as with MCF-7/17. These experiments show that the presence of CAS antisense reduces the sensitivity of MCF-7 cells towards PE.

Figure 2C:
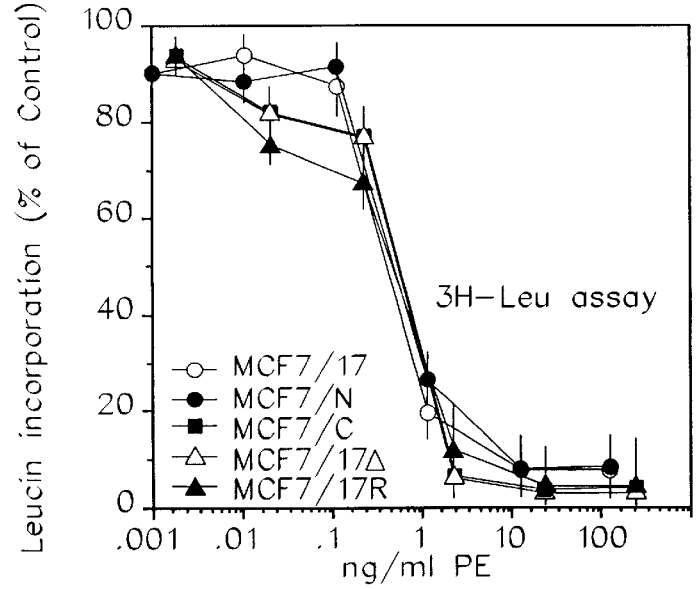

FIG. 2C shows inhibition of protein synthesis, assayed by measuring the incorporation of $^3$H-leucine 20 hrs after toxin addition. All cells tested showed the same amount of inhibition of protein synthesis indicating that the PE entered the cells and inactivated EF2, its normal cellular target.

Figure 2D:
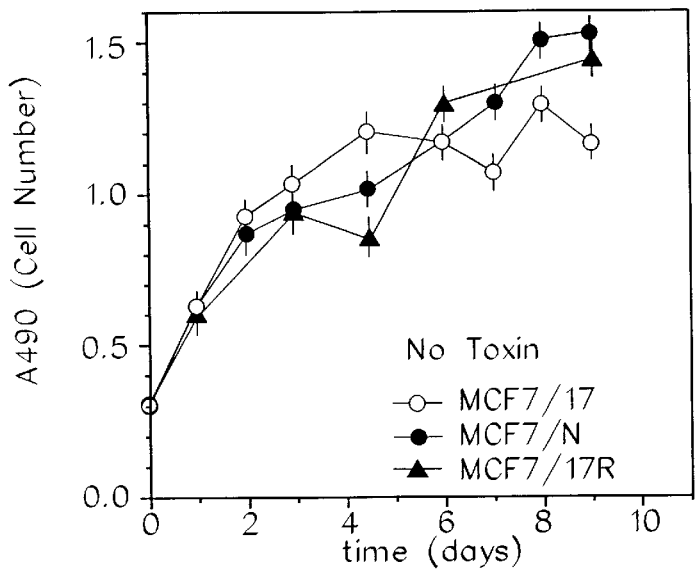
Figure 2E:
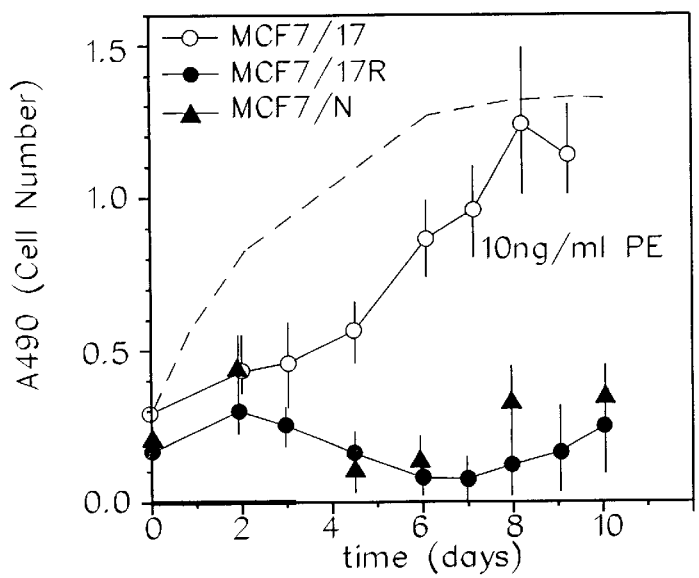
Figure 2F:
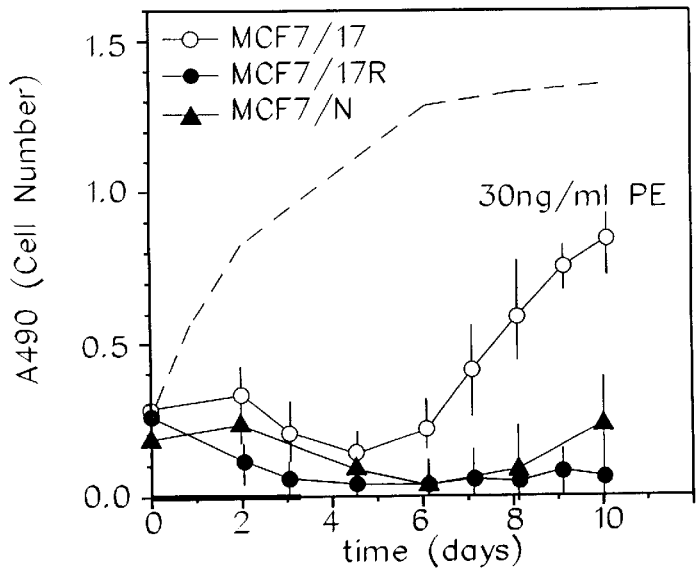

FIGS. 2D–F show time course experiments in which transfectants containing antisense CAS undergo growth arrest upon toxin treatment but recover after removal of toxin. Cell viability was determined by MTS assays in 96-well plates where A49D is proportional to the number of cells in each sample. MCF-7/17 cells, producing CAS antisense, showed growth about equal to that of the control cells, but a longer lag-phase before resuming growth after trypsinization. In FIGS. 2E and 2F, a typical growth curve of cells without toxin (representing the mean of three experiments) is indicated by a broken line and the duration of toxin exposure is indicated by a bar on the X-axis.

EXAMPLE 3

Cells Made Resistant to Toxin-Induced Apoptosis by Antisense CAS Expression Still Have Toxin-Altered Elongation Factor-2 (EF2)

The results shown in FIG. 2C indicated that PE altered EF2 is the treated cells whether or not the CAS gene was present or transcribed in the sense or antisense orientation. This was directly confirmed using an ADP-ribosylation assay.

Extracts for assaying ADP-ribosylation of EF2 by PE were prepared by suspending PBS-washed cell pellets in lysis buffer (10 mM Tris, 10 mM KCl, 1.5 mM Mg-acetate, 6 mM mercaptoethanol, pH 7.5) for 30 min at 20° C. followed by homogenization. The 0.2 vol 1.25 M sucrose was added, the suspension was centrifuged (30 min, 4° C., 100,000×g) and the supernatant was dialyzed against lysis buffer containing 0.25 M sucrose. Equal amounts of protein in extracts were incubated in 250 μl (final vol, adjusted with 50 mM Tris, 1 mM EDTA) assay buffer containing 40 mM DTT, with 1.5 μl $^{14}$C-NAD (Amersham, 287 mCi/μMole, 260 μCi/ml) and 10 ng/ml PE (final conc.) for 30 min at 37° C. Protein-associated radioactivity was precipitated with 12% TCA, and then washed with 6% TCA. The pellet was solubilized with 0.1 M NaOH, neutralized with HCl and radioactivity was determined by counting disintegrations per min in scintillation liquid.

As shown in FIG. 2C, there was no difference in the incorporation of $^3$H-leucine between MCF-7 cells containing CAS antisense and the control cell lines, even though the MTS assay showed that the toxin sensitivity was very different between these cell lines. In these experiments, an additional control cell line which contained CAS expressed in the sense direction (called MCF-7/R) was included; it showed identical results as the experimental cells for $^3$H-leucine incorporation after PE treatment.

The direct measurement of the ability of PE to ADP-ribosylate EF2 in extracts of CAS antisense MCF-7/17 cells and in control cells shown that the sensitivity of EF2 in the toxin resistant transfectant was indistinguishable from controls (see Table 1). Thus, CAS antisense does not make cellular EF2 resistance to PE. The EF2 becomes modified as effectively in cells containing CAS antisense as in control cells.

TABLE 1

The immediate actions of PE and TNF are not affected in CAS antisense containing cells (PE)

|  |  | MCF-7, MCF-7/N (control) | MCF-7/17 (CAS antisense) |
|---|---|---|---|
| PE | ADP-ribosylation activity (cpm) | 1328 ± 250 | 1329 ± 200 |
|  | protein synthesis inhibition (IC$_{50}$) (ng/ml) | 0.5–1 | 0.5–1 |
|  | cell death (LC$_{50}$) (ng/ml) | 1–2 | 15–20 |
| TNF | receptors/cell | 17000 ± 4000 | 17000 ± 5000 |
|  | affinity (pM) | 102 ± 8 | 104 ± 17 |
|  | cell death (LC$_{50}$) TNFα (ng/ml) | 0.15 | 1–3 |
|  | cell death (LC$_{50}$) TNFβ (ng/ml) | 1–3 | 20–30 |

ADP-ribosylation of EF2 in cell extract was assayed as described above. Inhibition of protein synthesis was measured by incorporation of $^3$H-leucine 15 hrs after toxin exposure, and cell death was assessed by MTS assays (see FIG. 2). The IC$_{50}$ is the toxin concentration that reduces protein synthesis by 50% compared to untreated cells and LC$_{50}$ is the concentration that kills 50% of the cells (as measured in MTS assays). The number of TNF receptors per cell and affinity was determined by $^{125}$I-TNF alpha (Amersham) competition and displacement assays using the program "Ligand" for data processing (Munson, P. J., and Rodbard, D., Meth. Enzymol, 82:543–576, 1983). The mean of these experiments +/−S.E. is shown; within this error range, displacement assays gave slightly lower apparent receptor number and higher affinity than the mean and competition assays lower affinity and higher reception numbers.

Figure 3:
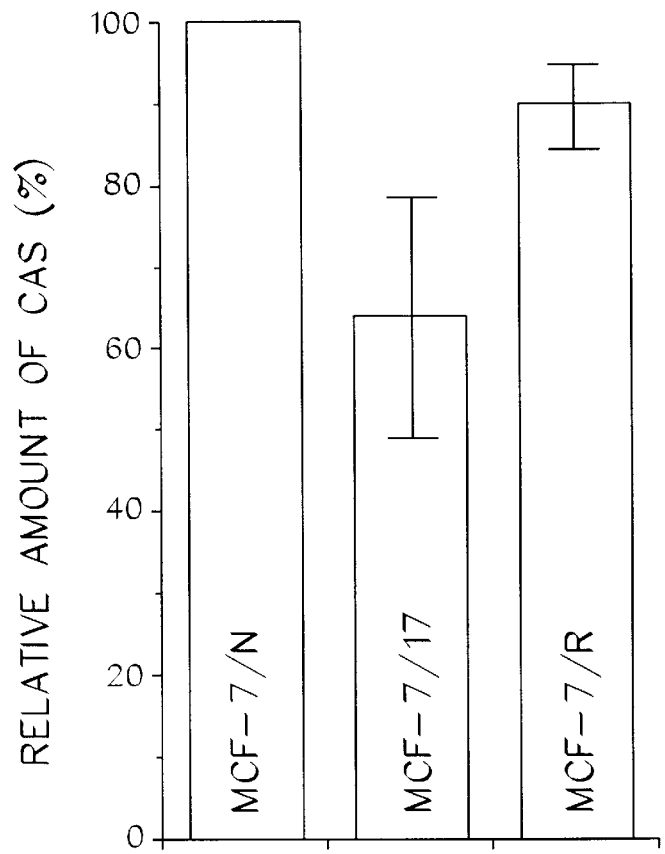
FIG. 3 shows that the relative amount of CAS protein detected in MCF-7 cells containing the CAS antisense clone (MCF-7/17) was reduced compared to that detected in MCF-7 cells containing the CAS sense clone (MCF-7/R) and control MCF-7 cells without a CAS clone (MCF-7/N).

Thus, the mechanism by which the cells containing CAS antisense become resistant is "downstream" of the primary damage done to the cells by the toxin. One explanation for the observed protective effects of the CAS antisense plasmid on cells is interference with expression of the corresponding cellular gene. To evaluate this possibility, we examined the levels of CAS protein in MCF-7 cells containing the CAS antisense clone (pCDM/HE17; labeled MCF-7/17 on FIG. 3), containing the CAS sense clone (pCDM/HE17R; labeled MCF-7/R on FIG. 3) and control cells without a CAS clone (labeled MCF-7/N on FIG. 3). Using standard Western immunoblotting techniques (Sambrook, J., et al., Molecular cloning, A Laboratory Manual, 2nd ed., 1989) and CAS-specific polyclonal antibodies (see Example 13 for details on antibody preparation), we found equal amounts of a CAS protein (of expected size about 100 kDa) in MCF-7/N and MCF-7/R cells, and reduced amounts in MCF-7/17 cells. FIG. 3 shows that CAS protein in cells containing the CAS antisense clone was detected in reduced amounts equal to about 65%±15% of that detected in the control MCF-7 cells. This result shows that the presence of CAS antisense reduces the intracellular levels of the CAS gene product.

EXAMPLE 4

Growth of Toxin Treated Cells Made Resistant to Toxin-Induced Apoptosis By Antisense CAS Expression To gain more information about the status of the cells that are resistant to PE, time course experiments were carried out at two concentrations of PE (10 and 30 ng/ml). These concentrations were chosen because they had maximal inhibitory effect on the growth of control cells (see FIG. 2A) and maximally inhibited protein synthesis (see FIG. 2C). In addition, cells containing sense plasmids as well as other controls were included. FIGS. 2D–2F show the time course of treatment with PE. The MCF-7/17 cells containing CAS antisense were treated with 10 ng/ml of PE for three days (see FIG. 2E) and showed little or not growth compared to untreated cells (compare to FIG. 2D). However, when the PE was removed the cells began to grow and by day 8 reached almost the same cell number as the control cells that were not treated with PE. FIG. 2F shows that MCF-7/17 cells that were treated with 30 ng/ml of PE for 3 days showed no growth, but after removal of PE, recovered and resumed growth. In contrast, MCF-7/N cells, which contained only the pMC1 neo/polyA plasmid, and MCF-7/17R cells which contained the pMC1neo/polyA plasmid and the pCDM/HE17R plasmid (CAS sense), showed no growth in the presence of 10 to 30 ng/ml of PE and did not recover after toxin removal (FIGS. 2E and 2F). This phenotype was also observed with the other control cell lines plasmids MCF-7/C and MCF-7/C2-C5.

These results show that cells containing the CAS antisense plasmid remain alive and being to proliferate when the toxin is removed, in contrast to control cells which die as a consequence of toxin treatment. The results also show that the effect of the antisense plasmid is specific because cells containing the sense plasmid (MCF-7/17R), as well as other control plasmids, did not recover after toxin removal.

The morphology of cells exposed to toxins reflects the changes observed using the MTS and $^3$H-leucine incorporation assays. Cells were exposed to PE and TNF and the morphology of the cells was observed by phase contrast microscopy of a random field (at 250× magnification) after incubation with PE (10 ng/ml) or TNF alpha (1 ng/ml) for 3 days. Control cells (MCF-7/N) become rounded, refractile and detach from the plate surface indicating cellular death. The MCF-7/17 cells transfected with the CAS antisense plasmid remained attached to the plate surface.

The morphologic appearance of MCF-7/N cells and MCF-7/17 cells (containing the antisense plasmid) was observed without toxin treatment and after treatment with 10 ng/ml of PE for two days. The untreated cells grow as flattened cells in islands characteristic of MCF-7 cells. There was no obvious morphological difference between the MCF-7/N cells and MCF-7/17 cells. However, the appearance of the cells treated with 10 ng/ml of PE for two days was very different. No MCF-7/N cells were detected attached to the dish; all the cells were floating, refractile and many were disintegrating. In contrast, most of the MCF-7/17 cells remained flattened and attached to the dish and resembled cells that had not bee treated with PE. This morphology occurred under conditions where the cells' ability to incorporate $^3$H-leucine into protein was arrested to background levels (see FIG. 2C at 10 ng/ml PE). This normal morphology was consistent with the cells' ability to resume growth when the toxin was removed (see FIGS. 2E and 2F).

EXAMPLE 5

DNA Degradation is Decreased in Cells Made Resistant to Toxin-Induced Apoptosis by Antisense CAS Expression Some cells undergo apoptosis upon exposure to ADP-ribosylating toxins (Kochi, S. K., and Collier, R. J., *Exp. Cell Res.* 208:296–302, 1993; Chang, M. P., et al., *J. Biol. Chem.* 264:15261–15267, 1989; Morimoto, H., and Bonavida, B., *J. Immunol.* 149:2089–2094, 1992). Because MCF-7 cells containing the CAS antisense plasmid become less sensitive to ADP-ribosylating toxins without changing their susceptibility to toxin-mediated protein synthesis inhibition, it is likely that the CAS antisense effects the susceptibility of cells to undergo apoptosis. One hallmark of apoptosis is nuclear DNA degradation and the formation of a DNA ladder due to internucleosomal cleavage of chromosomal DNA (Compton, M. M., *Cancer Metast. Rev.* 11:105–119, 1992). Therefore, cells treated with PE were used as a source of DNA (from the medium and soluble cell fraction) which was analyzed as described by Kochi and Collier (*Exp. Cell Res.* 208:296–302, 1993). Release of DNA fragments into cell culture supernatant was analyzed by labeling cells for 20 hrs with $^3$H-thymidine (Amersham), then changing the medium and exposing cells to toxin as described (Kochi, S. K., and Collier R. J., *Exp. Cell Res.* 208:296–302, 1993). DNA release was assayed by measuring radioactivity in the medium and in the soluble fraction of cells and comparing that to the total radioactivity.

Figure 4:
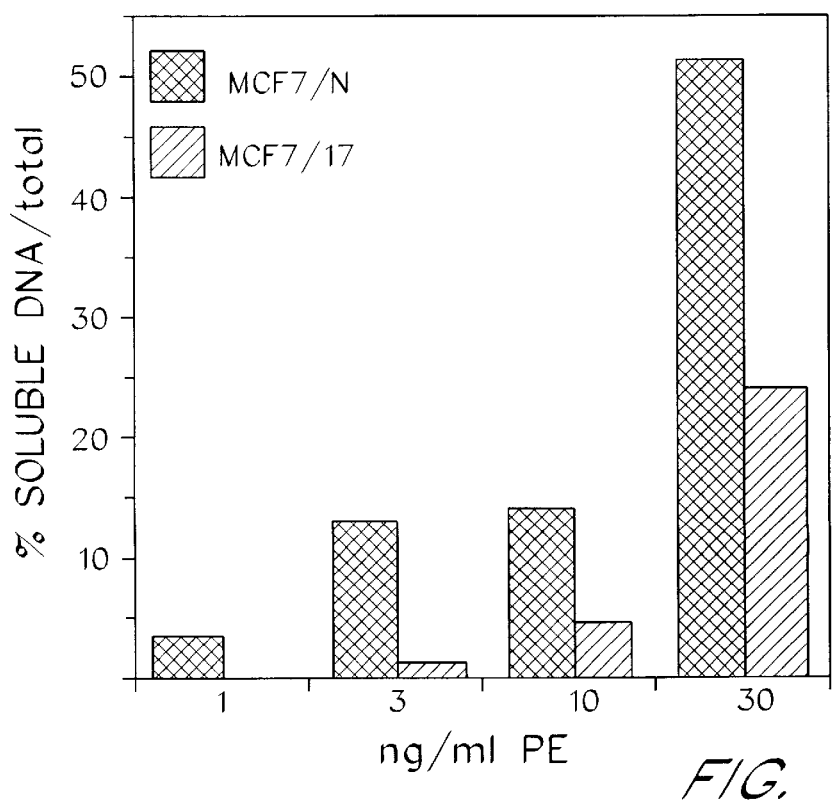
FIG. 4 shows that CAS antisense renders MCF-7 cells less susceptible to apoptosis as determined by degradation of chromosomal DNA which was assayed by release of $^3$H-containing DNA.

FIG. 4 shows that CAS antisense renders MCF-7 cells less susceptible to apoptosis as determined by nuclear DNA degradation. Toxin treatment induced degradation of chromosomal DNA as determined by two assays: radioactive measurement of degraded DNA present in the culture medium and visualization of the degraded DNA following gel separation.

To quantitate DNA degradation, $10^6$ cells were labeled with $^3$H-thymidine (1 mCi/ml) overnight and then treated with various amounts of PE for 15 hrs. The amount of $^3$H-thymidine in chromosomal DNA, the cellular soluble fraction and the medium was determined by scintillation counting as described (Kochi, S. K., and Collier, R. J., *Exp. Cell Res.* 208:296–302, 1993).

As shown in FIG. 4, with increasing concentrations of PE, there is a concomitant increase in DNA released into the medium and into the soluble fraction of cells. Because intact genomic DNA is usually not present in the culture medium and the soluble cell fraction of healthy cells, this indicates extensive DNA degradation upon toxin treatment of control cells. In contrast, in MCF-7/17 cells containing CAS antisense, the production of soluble DNA was greatly diminished at all PE concentrations tested (shown in FIG. 4).

The nature of the soluble DNA was determined by isolating DNA from the medium, which contained most of the soluble DNA, and subjecting it to electrophoresis and autoradiography to detect the size of soluble DNA (i.e., to detect a "ladder" characteristic of internucleosomal DNA degradation). When analyzing internucleosomal DNA degradation we found that DNA of cells still attached to culture dishes was in most cases a smear (50,000–200 bp) and the ladder fragments were difficult to visualize. However, DNA obtained from cell culture fluid by phenol/chloroform extraction and ethanol precipitation clearly showed a ladder. Therefore, DNA obtained from the medium was used to determine the extent of nuclear degradation and the sizes of the degraded DNA fragments. $^3$H-labeled DNA was isolated from the medium by phenol extraction and ethanol precipitation and separated by electrophoresis on a 1.5% agarose gel which was used to produce a autoradiograph.

The PE treated MCF-7/N cells displayed a typical nucleosomal ladder having wide bands of about 150–225 bp, about 300–425 bp, about 450–600 bp and in additional steps up to about 1500 bp. In contrast, the MCF-7/17 cells showed mostly higher molecular weight fragments (greater than 1500 bp) and a very faint DNA ladder of similar sizes as seen in the MCF-7/N cells but that was so faint it could not be photographically reproduced. Our finding that DNA degradation and nucleosomal ladder formation is diminished in MCF-7/17 cells containing CAS antisense suggests that toxin resistance is due interference with an apoptosis pathway.

EXAMPLE 6

Expression of Antisense CAS Makes Cells Less Susceptible to Apoptosis Induced by Tumor Necrosis Factors Alpha and Beta It is well established that apoptosis can be induced in certain cell lines by TNF alpha and TNF beta. The toxins PE and DT produce cell death by causing inhibition of protein synthesis by modification of EF2, whereas TNF acts by receptor a different mechanism involving binding and signal transduction (Smith, C. A., et al., *Cell* 76:959–962, 1994). Although two different mechanisms cause cell death, it has been suggested that DT-mediated and TNF-mediated cytotoxicity might share a common pathway leading to cell death (Morimoto, H., and Bonavida, B., *J. Immunol.* 149:2089–2094, 1992). Thus, if the pathway were part of the apoptosis machinery, one might expect that cells that are resistant to PE-induced apoptosis might also be more resistant to TNF-induced apoptosis.

TNF-binding was first demonstrated to show that MCF-7 cells express TNF receptors. Binding assays were performed essentially as previously described (Webber, K. D., *Mol. Immunol. in press*, 1995). $3 \times 10^5$ cells per dish in 24-well plates were chilled and blocked with RPMI/5% BSA/50 mM BES/50 mM BES pH 7 for 1 hr at 4° C. and washed twice with binding buffer (RPMI/1% BSA/50 mM BES, pH 7). $^{125}$I-labeled TNF alpha and cold TNF in binding buffer were then added and incubated for 2 hrs. For competition experiments, 80 pM final conc. of $^{125}$I-TNF, 12 nCi, 16 fmol/well (Amersham) was mixed with varying concentrations of unlabeled TNF. For Scatchard experiments serial dilutions, 18 to 70 pM, of labeled TNF were used. Labeled TNF was then removed and the cells were washed twice with binding buffer. Cell bound radioactivity was recovered in 0.5% SDS in TE and determined in a Beckman 5500B gamma counter. Receptor numbers and affinity was calculated using the LIGAND program (Munson, P. J., and Rodbard, D., *Meth. Enzymol*, 92:543–576, 1983). Table 1 and FIG. 5 shows that MCF-7 cells have TNF receptors and are sensitive to TNF mediated apoptosis.

Figure 5A:
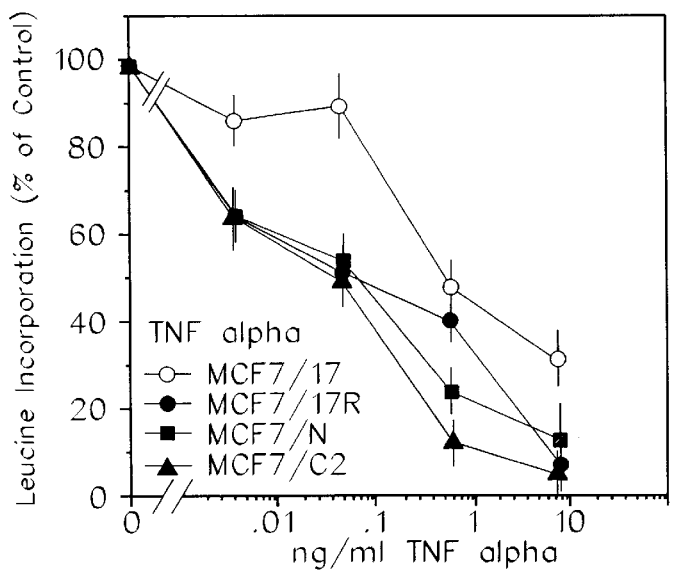
FIG. 5 shows that CAS antisense reduces the sensitivity of MCF-7 cells to TNF as determined by: $^3$H-leucine incorporation into cells treated with TNF alpha (FIG. 5A and 5B) and TNF beta (FIG. 5C); by cell growth over 9 days after treatment with TNF alpha (FIG. 5D) and TNF beta (FIG. 5E); and by TNF alpha receptor binding (FIG. 5F).
Figure 5B:
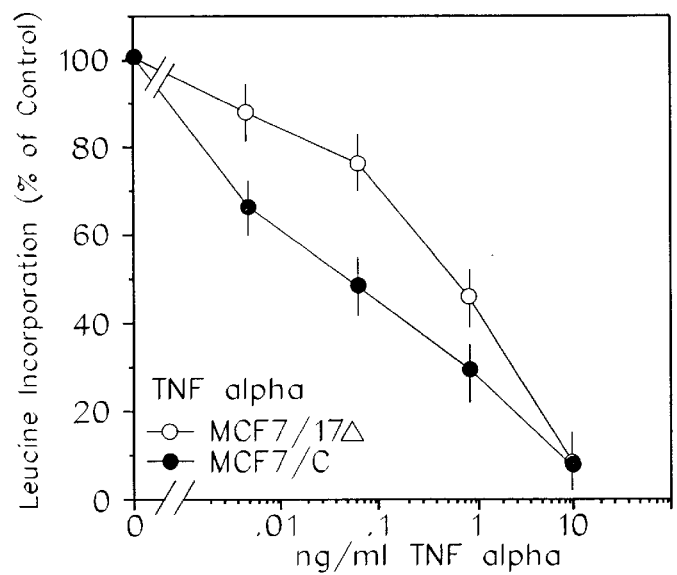
Figure 5C:
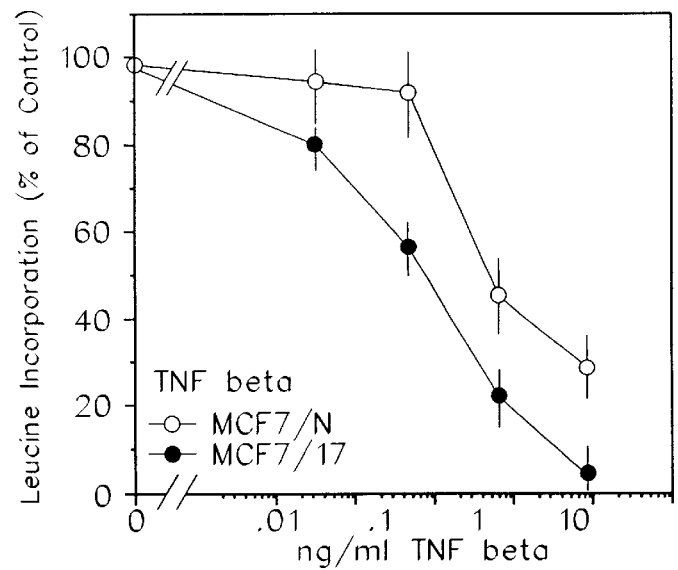
Figure 5D:
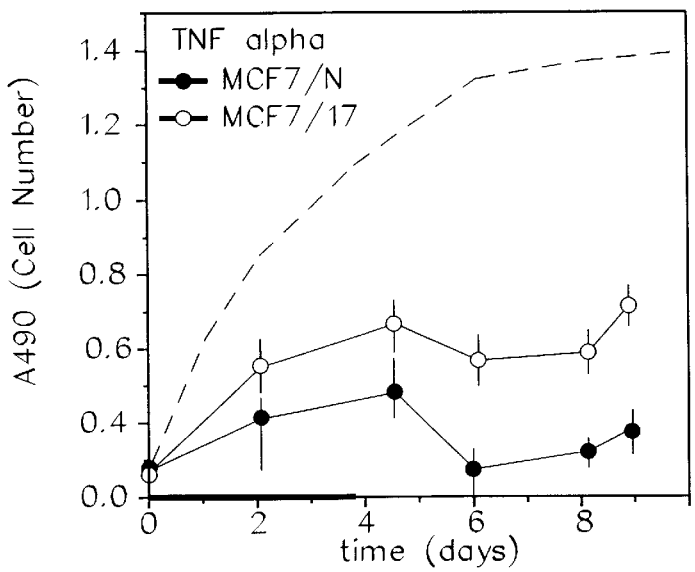
Figure 5E:
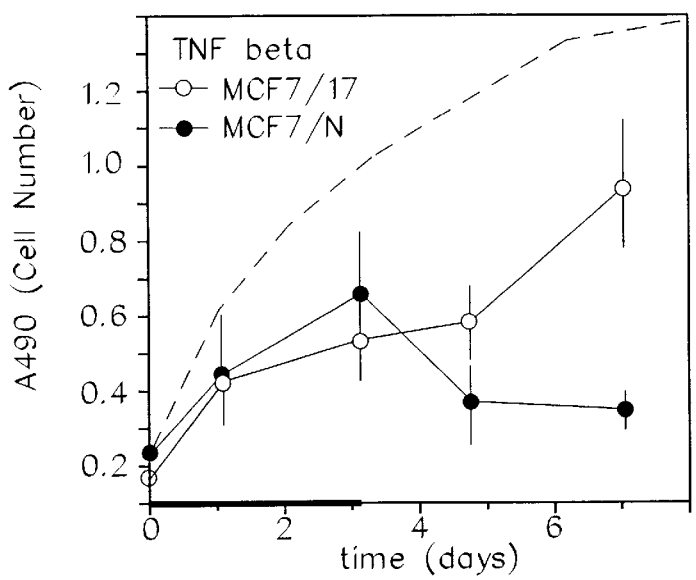

The effects of CAS antisense plasmids on TNF induced apoptosis in MCF-7 cells was then determined $^3$H-leucine incorporation assays were used to quantitate killing by TNF. The assays were performed 3 days after TNF alpha (FIGS. 5A and 5B) and TNF beta (FIG. 5C). FIG. 5 shows that CAS antisense reduces the sensitivity of MCF-7 cells to TNF. The IC$_{50}$ of TNF alpha on untransfected MCF-7 cells and cells containing control plasmids was approximately 0.1–0.2 ng/ml (FIGS. 5A and 5B). The IC$_{50}$ of TNF beta was 2–3 ng/ml for the control (FIG. 5C). In contrast, MCF-7/17 cells bearing the CAS antisense plasmid were about 5–10 fold less sensitive to both TNF alpha (IC$_{50}$ about 1 ng/ml) and to TNF beta (IC$_{50}$ about 20 ng/ml) (FIGS. 5A–5C).

This difference in TNF sensitivity between control cells and CAS antisense cells was also seen by examining the morphological appearance of TNF treated cells under phase contrast microscopy. Control cells treated with 1 ng/ml TNF were detached from the dishes and were disintegrating, while CAS antisense cells stayed attached to the dishes and resembled untreated cells. This phenotype was very similar to the effects seen with PE treated cells as described in Example 4.

Time course experiments were used to determine cell viability by MTS assays in 96 well plates as described in Examples 1 and 2. Similar to the phenotype of CAS antisense transfected MCF-7 cells that were treated with PE, TNF treatment of these cells produced growth inhibition, which was reversed after TNF removal (see FIG. 5D for TNF alpha and FIG. 5E for TNF beta, and compare to FIGS. 2D–F). An average growth curve (mean of three experiments) of cells without toxin is indicated by a broken line and the duration of TNF exposure is indicated by a bar on the X-axis. MCF-7/17 and MCF-7/17Δ contain CAS antisense. Controls were MCF-7/17R that contains the sense plasmid, MCF-7/C that contains the pCDM8 library vector without insert, and MCF-7/C2 that contains a randomly chosen library plasmid with an unknown insert (see FIG. 1B for comparison). The control cells did not survive TNF treatment and did not recover after TNF removal.

Figure 5F:
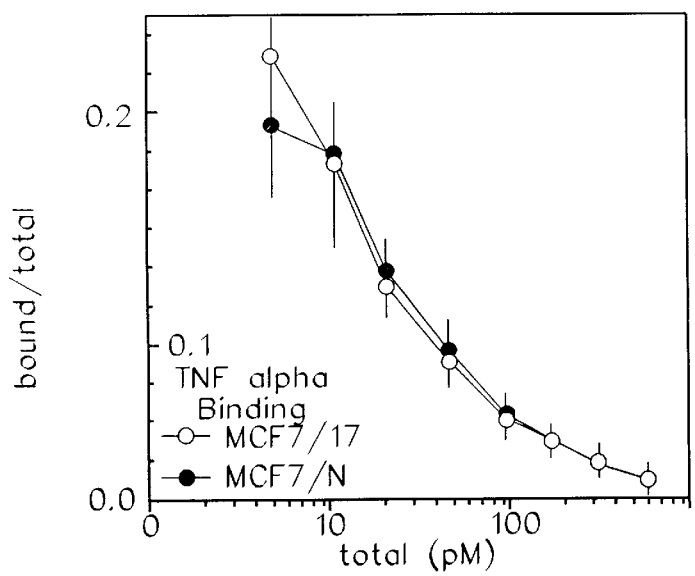

The altered sensitivity of cells to TNF when the CAS antisense plasmid was present was not due to interference with the immediate action of TNF, which is binding to its receptor. FIG. 5F and Table 1 show that the TNF receptor numbers and affinity remained unchanged in MCF-7/17 cells containing CAS antisense.

EXAMPLE 7

The DNA Sequence of a Complete CAS cDNA Reveals Homology to the Yeast Chromosome Segregation Gene CSEI The CAS antisense plasmid that reduces the sensitivity of cells to PE, DT and TNF contained only a 436 bp fragment of a CAS cDNA. To obtain a complete (normal human) CAS coding sequence, we used the cDNA insert of pCDM/HE17Δ as a probe to screen a human placenta cDNA library in lambda gt11.

$1 \times 10^6$ plaques of a Lambda gt11 cDNA library from placenta polyA RNA (Clontech™) were screened by hybridization with a radioactivity labeled cDNA insert of pCDM/HE17Δ using standard techniques (Sambrook, J., et al., *Molecular cloning. A Laboratory Manual*, 2ed., 1989). The largest inserts, about 2.4 kb, included the 3'-end but not the 5'-end of the cDNA with an estimated size of 3.2 kb.

Although several cDNA inserts were isolated, the longest being about 2.4 kb, no full length clone was obtained. A full length clone was expected to be about 3.2 kb from the mRNA size in Northern blots (discussed in detail in Example 8 and shown in FIG. 7). This size was also expected if the CAS cDNA were about the same size as the yeast CSE1 cDNA.

Because all of the isolated clones were from the 3' and the cDNA, the 5' end of the cDNA was obtained by the RACE method (Apte and Siebert, *Biotechniques* 15:890–93, 1993; Frohman et al., *Proc. Natl. Acad. Sci. USA* 85:8998–9002, 1988) using 5'-RACE-Ready™ placenta cDNA (Clontech) as template and the Clontech anchor primer 5'. CTGGT TCGGCCCACCTCTGAAGGTTCCAGAATCGATAG-3' (SEQ ID NO:3) and a CAS specific primer 5'. TAATGAGGTCTCTCACAAA-3'(SEQ ID NO:4) positioned 160 bp downstream of the 5' end of the longest lambda insert. Amplification was done for 30 cycles (2 min at 94° C., 2 min at 60° C., 2 min at 72° C. and a final extension of 10 min at 72° C.) using a Perkin Elmer GeneAmp XL™ PCR kit. A single 1160 bp fragment was obtained which was the correct 5' end of the CAS because the overlap of this fragment 3' end matched with the first 160 bp of the longest previously obtained lambda clone 5' end. The lambda fragments and RACE fragments were cloned into pCRII (Invitrogen) and sequenced with an ABI™ 373A sequencer and ABI Dye-Deoxy Terminator™ kit.

The nucleotide sequence of the cDNA clone is SEQ ID NO:1 (GenBank acces. no. U33286), and deduced amino acid sequence of the CAS protein is SEQ ID NO:2, as shown in FIG. 6A and FIG. 6B. The CAS cDNA from HeLa used as a screening probe had the same sequence as the human placenta cDNA an corresponds to nucleotides 2100–2536 of the full-length clone. The coding regions of human CAS and yeast CSE1 (Xiao, Z., et al., *Mol. Cell. Biol.* 13:4691–4702, 1993) are of approximately the same size, 971 and 960 amino acids respectively, and their sequence is similar over their whole length with some small gaps, resulting in overall homology of about 59%. The deduced translation products have approximately the same size and are homologous as determined by performing homology analysis and motif searches using the Genetics Computer Group package version 8 (Madison, Wis.) of the BLAST (Altschul, S. F. et al., J. Mol. Biol. 215:403–410, 1990) analysis with the National Center for Biotechnology Information network service. The overall homology (protein similarity) is 59% and in some portions, the homology is greater than 75% with about 50%identity. For example, CAS protein sequence showed identity with the CSE1 protein sequence over amino acid stretches of 11 amino acids (in one region), 9 amino acids (in one region), 8 amino acids (in one region), 7 amino acids (in one region), 6 amino acids (in two region) and regions of 5 or fewer identical amino acids in the aligned sequences. No defined protein other than CSE1 showed significant homology to CAS. However, some previously sequenced but functionally undefined short expression sequence tags ("EST" sequences) of between 209 and 346 bp were found to have homology or to match identically to the 5' or 3' end of CAS cDNA. There was no significant protein sequences motif in the CAS sequence that would indicate its molecular function although some short sequence stretches are similar in motif to phophorylation sites of protein kinases ERK1 and ERK2 or the transcription factor TFIID, to basic regions (amino acids 372–385) that may be involved in nuclear localization or DNA binding, and to zinc-finger proteins (amino acids 613–630).

The homology of the CAS gene relative to the yeast CSE1 gene shows that these are conserved genes and therefore the proteins encoded by these genes are likely to have similar important cellular functions. For comparison, the yeast CSE1 is an essential gene involved in cell division (i.e., homozygous CSE1 mutations are lethal; Xiao, Z., et al., *Mol. Cell. Biol.* 13:4691–4702, 1993). However, the function of the human CAS gene in the process of apoptosis, as defined by the results in Examples 3–6, differs from that described for the CSE1 gene in yeast.

EXAMPLE 8

Expression of CAS in Normal Human Tissues and Human Cancer Cell Lines

To determine if CAS may have a role in cell proliferation as well as apoptosis, the expression of CAS in human tissues and in tumor cell lines was analyzed in Northern blotting (Sambrook, J., et al., *Molecular cloning. A Laboratory Manual.*, 2ed., 1989). Northern blots containing about 2 µg polyA-containing mRNA of various tissues separated on a denaturing formaldehyde 1.2% agarose gel (Clontech) were hybridized with radioactive labeled CAS probe (insert of pCDM/HE17Δ; $^{32}$P random primed, about $10^8$ cpm/µg) or actin and/or GAPDH control probes (Clontech) having comparable specific activities for 20 hrs at 50° C. in Hybrisol 1™ (50% Formamide, Oncor) solution. Blots were exposed to Kodak XAR2™ film (−70° C. with screen) for 18–20 hrs (to detect CAS) or about 6 hr (to detect actin and GAPDH), and then scanned on a Molecular Dynamics Phosphoimager 425™. RNA levels were quantitated by comparing the signals of CAS to the actin and/or GAPDH signals.

The control hybridizations showed that approximately equal amounts of RNA were loaded for most tissues except for skeletal muscle which could not be exactly quantitated due to additional actin band and apparently elevated GAPDH. Some tissues were tested in duplicate to demonstrate the reproducibility of the results.

Figure 7:
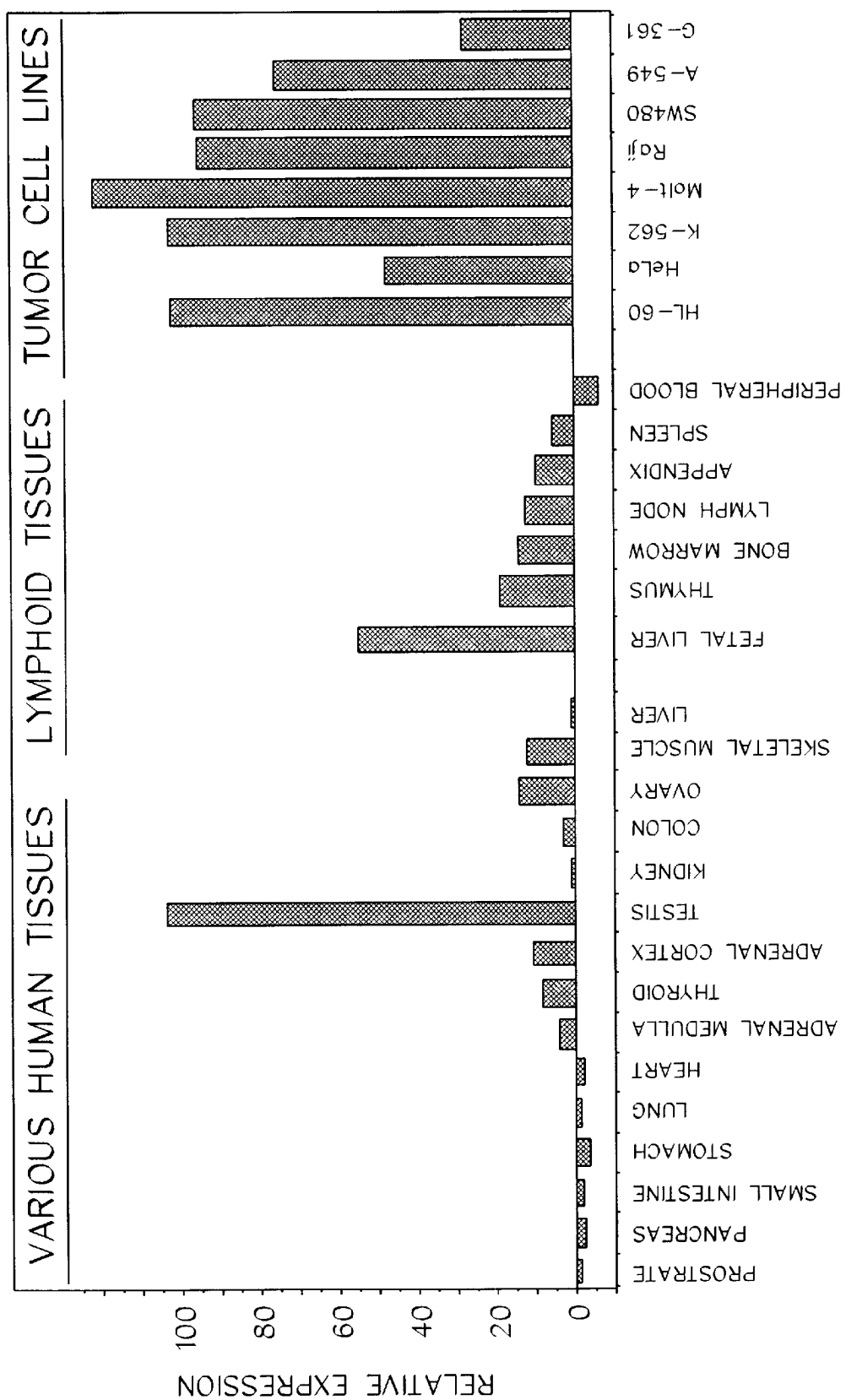
FIG. 7 shows the relative expression of CAS in human tissues and some cancer cell lines, as measured by Northern blots, from which the relative mRNA levels in tissues and tumor cell lines were determined.

The CAS mRNA, detected band of about 3 kb, was found in many tissues including pancreas, adrenal medulla, thyroid, adrenal cortex, testis, thymus, small intestine, stomach, spleen, lymph node, thymus, appendix, peripheral blood, bone marrow, fetal liver, spleen, prostrate, ovary, colon, heart, brain, placenta, lung, liver, skeletal muscle and kidney. A quantitiation of CAS expression, normalized to the expression of actin or GAPDH is shown in FIG. 7. Relative mRNA levels in tissues and tumor cell lines were determined by comparing the CAS intensities with the mean of actin and GAPDH signals using a Molecular Dynamics Phosphoimager™. For determining "relative expression" the CAS/Control ratio found in most tissues (the mean of levels found in prostrate, small intestine, colon, heart, brain, lung and pancreas) was defined as a "basal level" and were set to 1. Testis, which is the tissue having the higher expression level, was set to 100. The others were determined relative to these tissues.

Expression was high in testis and fetal liver which contained many actively proliferating cells, and was elevated (above basal level) in tissues that contained some proliferating cell, e.g. lymphoid tissues. Expression was slightly elevated in skeletal muscle. Very low expression was detected in peripheral blood which does not contain proliferating cells.

In addition, various proliferating tumor cell lines, e.g. SW480 (colon), A549 (lung) and HL60, K562, Molt4 and Raji (leukemias and lymphomas) contained high levels of CAS mRNA.

Based on these results, expression of CAS can be used as a marker for cell proliferation. Because cell proliferation is a hallmark of cancer cells, detecting CAS expression in cells above basal levels can serve as a method for detecting cancer cells.

EXAMPLE 9

The CAS Gene is Located in the 20q13 Region of Human Chromosome 20

To identify the chromosomal localization of the CAS gene, Southern blot hybridization of a CAS probe to a panel of somatic cell hybrids that represent the different human chromosomes in a mouse or hamster background was performed. Under stringent conditions, a 436 bp cDNA fragment covering the CAS cDNA from position 2100 to 2536 (see FIG. 6A) was hybridized to the panel.

A southern blot containing human (male and female) genomic DNA cut with PstI, mouse and hamster DNA, and genomic DNA from somatic cell hybrids containing single human chromosomes was obtained from ONCOR and hybridized under stringent conditions with the CAS probe. On the autoradiograph, mouse and hamster lines were easily distinguished because under these stringent conditions, hybridization of CAS to mouse DNA was easily seen, but no hybridization was detected to hamster DNA. The CAS probe hybridized to human female and male DNA and to DNA from the mouse cell line that carries a human chromosome 20.

Two PstI fragments of human genomic DNA specifically hybridized CAS probe as expected because the probe contained an internal PstI site. Thus as least two fragments would be expected when genomic CAS DNA is cut with PstI. Of the different somatic cell hybrids containing one human chromosome each (in mouse or hamster cell background), these two fragments were detected in the cell line that contained human chromosome 20. Thus, based on these hybridization results, CAS gene is located on chromosome 20.

To further the CAS gene, we localized the gene on human DNA contained in yeast artificial chromosomes (YAC). The center Centre d'Etude du Polymorphisme Humaine (CEPH) human YAC Megabase library (Cohen, D. et al. *Nature* 366:698–701, 1993) was screened by PCR using the primers P1 (5'GACATCCCGTCTTCCTATATG) (SEQ ID NO:5) and P2 (5'AAGAAGCCTCACTAGAGCAGGA) (SEQ ID NO:6) which bound to and amplified a 90 bp fragment when CAS cDNA and human genomic DNA were individually used as templates. One YAC clone, 953-B-4, was specifically amplified with these primers.

Microsatellite markers were identified on or near the YAC 953-B-4 address using techniques well known in the art and this information was used to position the CAS gene relative to typed microsatellite markers in the YAC library. YAC 953-B-4 overlaps with YACs positive for the genetic marker D20S176, which is mapped to the long arm of human chromosome 20, indicating that the CAS gene is located within a 2–3 Mb region of the genetic marker D20S176 on chromosome 20.

This position was confirmed by Fluorescent In Situ Hybridization (FISH; described in greater detail below) (Thompson, C. T. & Gray J. W., *J Cell. Biochem.* (SuppL) 17G:139–143, 1993) analysis P1 clone containing the human CAS gene as probe (see Example 10). This position is close to the 20q13 region that is amplified in certain breast tumors and breast cancer cell lines (e.g., HTB20), and in colon and bladder cancer cell lines. This region is known to contain amplifications that correlate with aggressive progression of breast caner and probably harbors one or more oncogene(s) responsible for the aggressive cancer phenotype (Tanner, M. M. et al., *Cancer Res.* 54, 4257–4260, 1994).

EXAMPLE 10

The CAS Gene is Amplified in Human Cancer Cell Lines

Because the CAS gene is located in a region known to undergo amplification in tumor cells, the amplification of the CAS gene was examined in a number of tumor cell lines using Southern blotting.

Quantitative Southern hybridizations were used to determine the relative number of copies of the CAS gene in genomic DNA of tumor cell lines using techniques well known to those skilled in the art (Sambrook, J., et al., *Molecular cloning. A Laboratory Manual.*, 2ed., 1989). Genomic DNA from a variety of cancer cell lines including breast, colon, bladder, gastric, ovary, prostate, melanoma, leukemia and lymphoma were tested. As shown in FIG. 7, the cells lines analyzed were BT-474 (also known as HTB20), MCF-7, LS174T, COLO205, SW-480 and N-87 (all of which are available from the American Type Culture Collection, Rockville, Md.). As an internal control, the actin gene was also hybridized to determine the normal gene copy number without amplification. This probe is an appropriate control also for cell lines which are described to be aneuploid, because chromosome 7, which harbors the actin gene, is over-represented in breast cancer cell lines (HTB20). Therefore, this control probe gives a very conservative estimate of the CAS amplification (because it can already be elevated itself) and compensate potential over-representation of chromosome 20 in aneuploid cell lines.

FIG. 8 shows the comparison of the ratio of the hybridization signals between control signal and CAS signal in different cell lines hybridized with CAS probe and actin control probes. The ratio between CAS and actin control signals was determined quantitatively scanning the bound radioactivity on the Southern blots using a Phosphoimager™. Human genomic DNA was used as a reference for single copy status of CAS (the actin/CAS signal ratio was set to 1 for human genomic DNA).

Figure 8A:
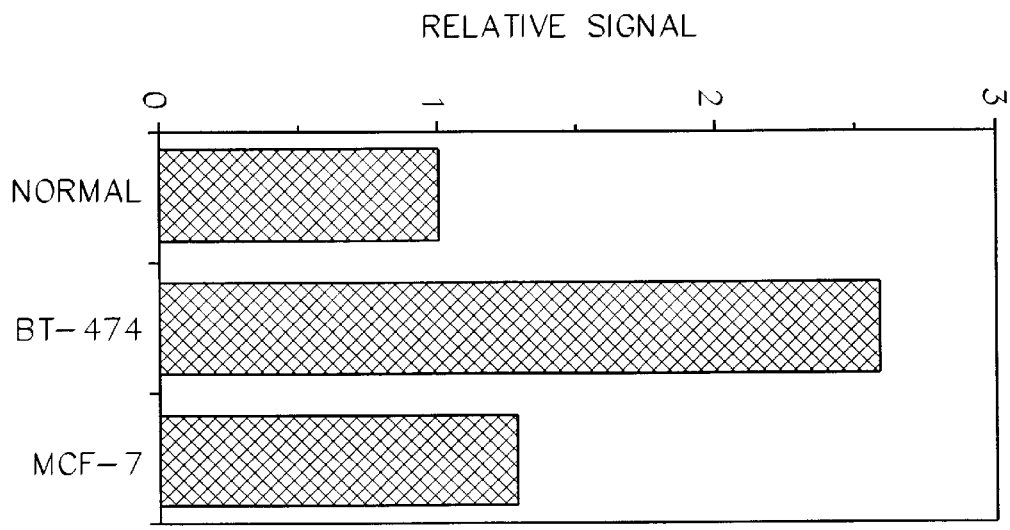
FIGS. 8A and 8B shows the copy number of the CAS gene detected in various cancer cell lines.
Figure 8B:
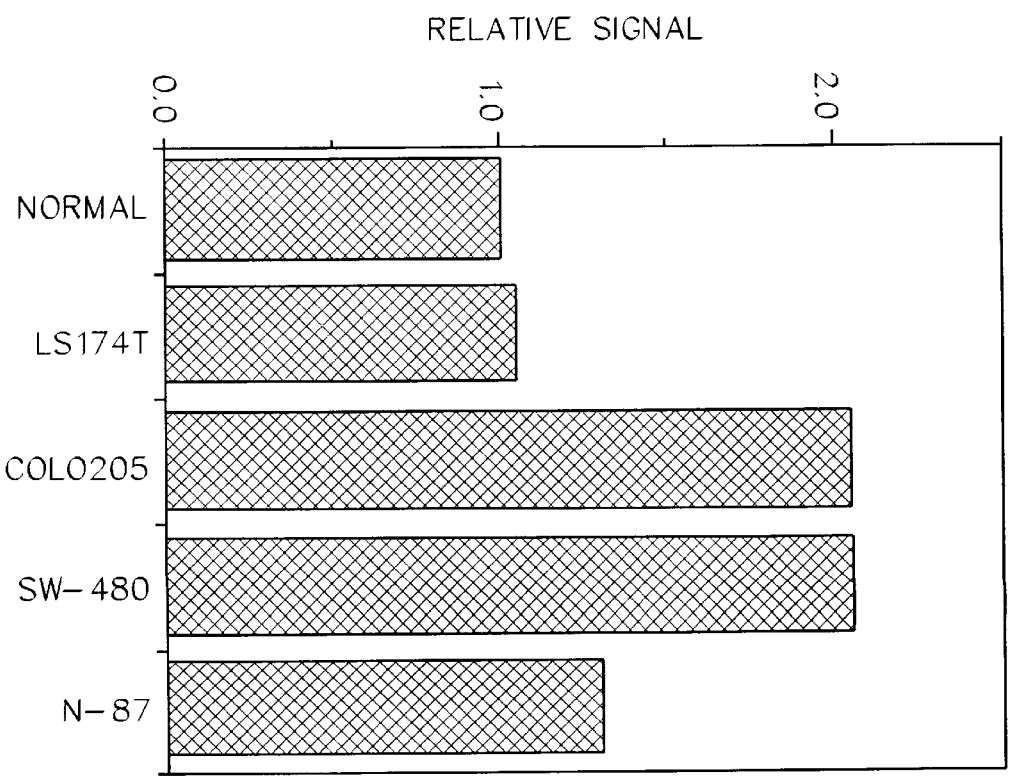

The ratio for normal human genomic DNA 1 and the other samples are relative to that. If one assumes a linear relation between gene targets on the filter and hybridization signal, this ratio approximates the copy number of CAS. The results shown in FIG. 8A show that the CAS gene is amplified in the breast cancer cell line BT-474 (HTB20), and colon cancer cell lines COLO205 and SW-480 when compared to the normal human genomic DNA controls and to cancer cell lines MCF-7 (breast cancer), LS174T (colon cancer) and N-87. FIG. 8A shows the results for two breast cancer cell lines and FIG. 8B shows the results for colon cancer cell lines (SW480, COLO205, LS147T) and a gastric cancer (N87) cell line. The CAS gene was also amplified about 2-fold in the colon cancer line COLO201 and the leukemia cell line CEM, although there was no amplification of CAS found in three other leukemia cell lines (K562, HL60 and KG1) (date not shown).

The CAS gene was amplified in the breast cancer cell line HTB20 which was previously described to contain a 20q13 amplification. In contrast, the CAS gene was not amplified in a cell line (MCF-7) that does not contain the described amplification.

The 20q13 region that is found to be amplified in certain cancers and cell lines is not a homogenous region but consists of different regions that lie close together and contain various degrees of (possibly independent) amplifications. For example, Tanner et al. (*Cancer Res.* 54, 4257–4260, 1994) defined one minimal high amplification region, but also noted surrounding regions being amplified to a lesser degree, and different amplifications in different breast cancer cell lines. Although a close link of the CAS gene to the minimal amplification region in 20q13 has been established by the YAC localization (see Example 9), more detailed information about CAS amplification in cancer cells was obtained by FISH analysis (Thompson, C. T. & Gray, J. W., *J Cell. Biochem.* (SuppL) 17G:139–143, 1993) using the P1/hCAS clone (see Example 11) on BT474 breast caner cells which showed CAS amplification in quantitative Southern hybridizations.

Interphase and metaphase chromosomes were hybridized with digoxigenin-dUTP-labeled P1/CAS and biotin-dUTP labeled control probes P1/2672 and P1/2567 (Genome Systems; located close to CAS on 20q) or P1/5461 (Genome Systems; located on the 20p arm). The control clones P1/2672 and P1/2567 were mapped by Genome Systems previously at about 2 Mb centromeric (for P1/2672) and telomeric (for P1/2567) from CAS on chromosome 20 or on 20p (for P1/5461). P1/CAS was visualized by fluoresceinanti-digoxigenin antibody (green) and the controls Texas Red-avidin (red) using a triple band pass filter set at DAPI counterstain.

FISH analysis showed that CAS was amplified 74 fold (up to 14 copies per cell) in these cells and also that the CAS gene sequence was translocated from the 20q13 locus to various other unidentified chromosomal locations.

To analysis whether CAS is amplified in other cancer cell lines in addition to the than breast cancer cell line, we analyzed Southern blot hybridization genomic DNA from three cell lines derived from colon cancer (COLO205, LS174T and SW480) and one gastric cancer cell line (N87). Again, human genomic DNA was used as a single copy CAS reference control. FIG. 8B shows that DNAs of the colon cancer cell lines SW480 and COLO205 had stronger CAS signals than human genomic DNA. The other cell lines showed approximately the same CAS signal. The quantitation of the Southern hybridization signals by Phosphoimager™ analysis indicated a 2-fold amplification of CAS DNA in the colon cancer cell lines COLO205 and SW480. Thus, CAS is amplified not only in cell lines of breast cancer but also in other types of cancer including two out of three colon cancer cell lines that were analyzed. FISH analysis showed that this amplification in color cancer cells was not due to specific amplification of CAS DNA alone. Instead, in these cells, the entire chromosome 20 or a larger portion of the chromosome (e.g., the 20q arm) was amplified.

P1/CAS contains most (and probably all) of the CAS gene because: (1) PCR primers for the 5' portion and 3' portion of the cDNA amplify 5' and 3' CAS gene fragments when using P1/CAS as template; (2) 5'- and 3'-end cDNA probes hybridized to P1/CAS; and (3) DNA sequencing reveals the presence of the CAS coding region in that phage. P1/CA was labeled with digoxigenin and hybridized to interphase and metaphase chromosomes and detected with fluorescein-labeled anti-digoxigenin antibodies. As reference probes for the determination of the relative amplification status of CAS, we used the following biotin-labeled P1 clones: P1/2672, which hybridizes on 20q, centromeric to the position of the CAS gene in 20q13; P1/2567, which is telomeric to CAS; and P1/5461, which maps to the p arm of chromosome 20. The normal cell control (peripheral blood lymphocytes or PBL) showed two copies with each probe on the long arm of chromosome 20. Metaphase chromosomes showed a linear orientation with P1/2672 located centromeric and P1/2567 located telomeric to P1/CAS. These results confirmed the position of P1/CAS on 20q13 as defined YAC mapping.

CAS in Breast Cancer Cells. We then analyzed five breast cancer cell lines: BT-474, MDA-MB-157, UACC-812, MDA-MB-361, and MDA-MB-134. BT-474 was chosen because Southern analysis indicated potential CAS amplification. The others were evaluated because 20q13 amplifications occur frequently in breast cancer and because such amplifications were already demonstrated by comparative hybridization (CGH) and FISH with other probes in lines UACC-812, MDA-MB-157, and BT-474 (Tanner et al., Cancer Res. 54:4257–4260, 1994). On BT-474 cells, pair-wise hybridization showed 8 to 16 signals with P1/CAS but only two signals per cell with centromeric control probe. The two centromeric signals were linked to P1/CAS in a chromosome that appears to be the remainder of chromosome 20. Thus, relative to the region centromeric of CAS, as defined by the control phage (P1/2672), the CAS gene is amplified four to eight-fold. Pair-wise FISH on BT-474 cells with P1/CAS and P1/2567 (as a control that hybridizes telomeric of CAS) showed 8 to 12 signals (in one experiment, up to 18) with CAS and 4 signals with P1/2567. Two of the four control signals were linked to CAS; the others were found on another chromosome separated from CAS. BT-474 cells do not contain a normal chromosome 20 and all three probes hybridized to morphologically abnormal chromosomes. The amplified CAS gene was translocated to different abnormal chromosomes, each containing one to five copies of CAS. No double minute chromosomes were seen in BT-474 cells.

The other breast cancer cell lines that we analyzed, MDA-MB-134, MDA-MB-157, MDA-MB-361 and UACC-812 contained three to six copies of CAS, mainly present on abnormal marker chromosomes. MDA-MB-361 contained two normal copies of chromosomes 20 (with CAS) and one additional of CAS separated from the telomeric 20q control on an aberrant chromosome. These cells also had a third copy of the control gene separated from CAS on another abnormal chromosome. MDA-MB-134 cells contained four to five copies of CAS, two to three normal copies of chromosome 20, and two CAS genes on a 20q isochromosome. UACC-812 MDA-MB-157 contain three to six copies of CAS and of the centromeric control. Both signals were linked on abnormal chromosomes. UACC-812 cells contain abnormal chromosome 20 material with the centromeric control probe amplified to a higher degree than CAS (to five to eight copies), consistent with the observation of a second amplified region centromeric from CAS in this cell line (Tanner et al., Cancer Res. 54:4257–4260, 1994).

CAS in Colon Cancer and Leukemia Cells. Three colon cancer cell lines (SW480, COLO201 and COLO205) were identified as amplification candidates by Southern analysis and were analyzed by FISH with P1/CAS, to control probes described above, and another 20p probe (P1/5461). In SW480 and COLO205, CAS was located on aberrant chromosomes containing parts of 20q, similar to MDA-MB-157 and UACC-812 but in contrast BT-474 cells. The extra CAS copies were linked to 20q controls but separated from 20p. The elevated copy number that was apparent in Southern blots of COLO201 (colon and CEM(leukemia) cells is attributable to extras copies of chromosome 20. We found five copies of chromosome 20 per COLO201 cell and six to eight copies per CEM cell.

The results of these studies on CAS amplification in selected cancer cell lines are summarized in Table 2. The relative numbers of the CAS gene were determined compared to normal human peripheral blood lymphocytes (PBL) which have no amplification of the CAS gene (i.e., two copies of the CAS gene by FISH analysis in the 46 chromosomes per cell). All of the cell lines shown in Table 2 have some amplification of the CAS gene, often associated with some chromosomal abnormalities, such as an extra copy of chromosome 20 ("extra 20"), an aberrant chromosome 20 ("aberrant 20") such as no normal chromosome 20 but detection of 20q marker chromosomes, an amplification of the 20q region ("large 20q"), or a CAS-specific amplification and translocation to another chromosomal region than 20q ("CAS translocation").

TABLE 2

CAS Gene Amplification in Selected Cancer Cell Lines

| Cell Line | Cancer Type | CAS Copies (FISH) | Chromosomes per cell | Fold Amplification | Observations |
|---|---|---|---|---|---|
| MDA-MB-134 | Breast | 4 | 86 | <2 | |
| MDA-MB-157 | Breast | 2–6 | 54 | <3 | large 20q |
| UACC-812 | Breast | 3 | 60 | <2 | aberrant 20 |
| MDA-MB-361 | Breast | 3 | 56 | <2 | aberrant 20 |

TABLE 2-continued

CAS Gene Amplification in Selected Cancer Cell Lines

| Cell Line | Cancer Type | CAS Copies (FISH) | Chromo- somes per cell | Fold Amplifi- cation | Observations |
|---|---|---|---|---|---|
| BT-474 | Breast | 8–16 | 95–100 | 3–8 | aberrant 20; CAS translocation |
| COLO201 | Colon | 5 | 57–60 | ≈2 | extra 20 |
| COLO205 | Colon | 5 | 65–69 | ≈2 | extra 20; large 20q |
| SW480 | Colon | 4–6 | 48–55 | ≈2 | aberrant 20; large 20q |
| CEM | Leukemia | 6–8 | 83–86 | ≈2 | extra 20 |

Figure 9:
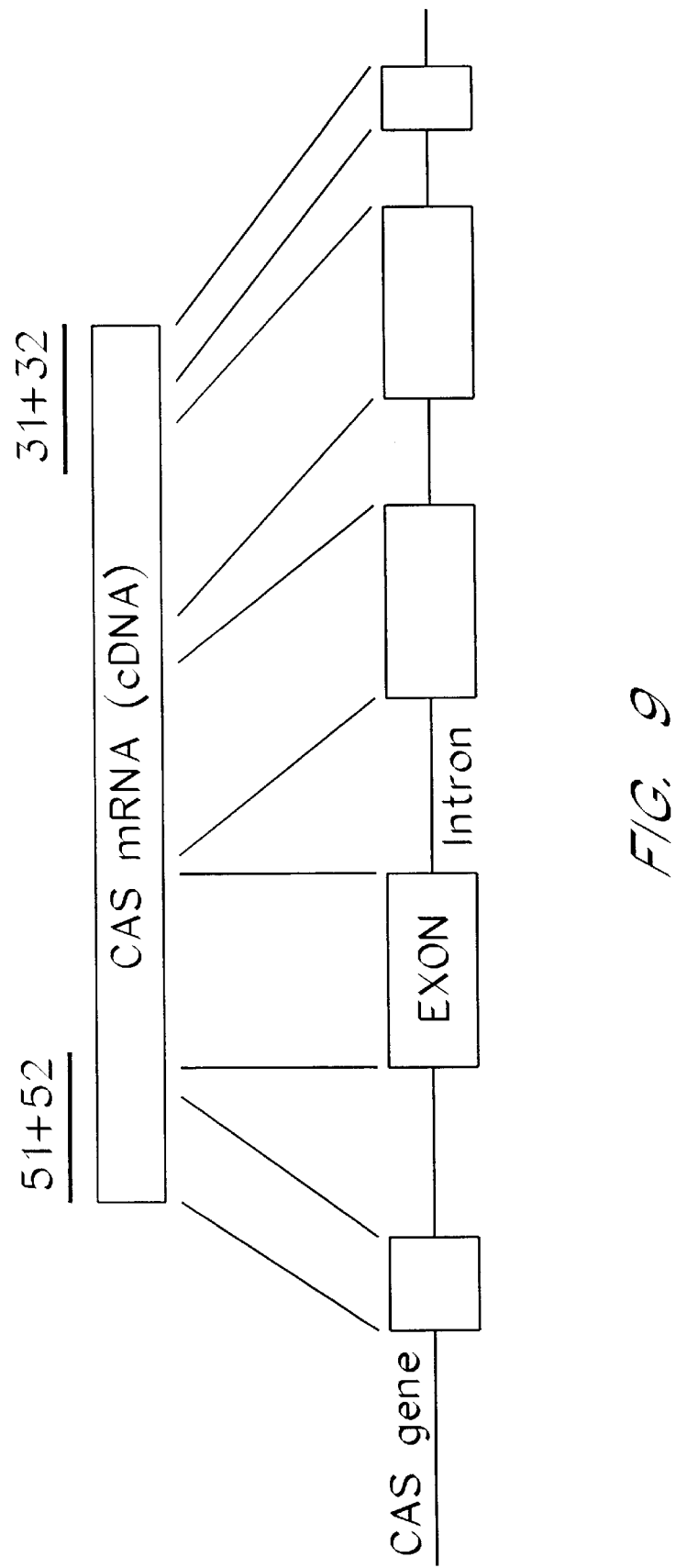
FIG. 9 shows the relative location of the CAS gene on 20q13.

FIG. 9 shows the relative location of the CAS gene on 20q13 relative to other markers on an ideogram adapted from Tanner et al. (*Cancer Res.* 54:4257–4260, 1994). The other markers are "GHRH" for growth hormone releasing factor; "RPN2" for riboporin 2; "SRC" for oncogene src; "TOP1" for topoisomerase 1; "ADA" for adenosine deaminase; "SEMG1" for seminogelin 1; "PTPN1" for protein tyrosine phosphatase, "MC3R" for melanocortin-3 receptor; "RMC20C001" for Tanner et aL's amplification probe; "PCK1" for PEP carboxykinase; "GNAS" for guanosine NT-binding protein; "CHRNA4" for cholergic receptor α-4, "EDN3" for endothelin 3; and "ZNF8" for zinc finger protein 8.

Because CAS is like other known oncogenes related to apoptosis and cell proliferation, and it is amplified in cell lines of breast and other cancers, the CAS gene may plays a role in cancer. Furthermore, because amplification of the 20q13 region in which the CAS gene is located correlates with aggressive breast cancer, the detection of CAS amplification or other alternations involving the CAS gene are valuable as a predictive factor in cancer diagnosis and therapy.

EXAMPLE 11

Isolation of Genomic Clone Containing the Human CAS Gene

A P1-clone containing the CAS gene, called P1/hCAS, was isolated from a human genomic P1-library by standard molecular biology and PCR techniques as described by Sternberg (*Trends in Genetics* 8:11–16, 1992). The PCR primers P1 comprising 5'GACATCCCGTCTTCCTATATG 3' (SEQ ID NO:5) and P2 comprising 5'AAGAAGCCT-CACTAGAGCAGGA 3' (SEQ ID NO:6) located in the human CAS cDNA, which amplify a 90 bp CAS-specific DNA fragment from human genomic DNA were used to identify a P1 clone from the P1-library of GENOME SYSTEMS that hybridized to these primers. This P1 clones was called P1/hCAS. Because the primers used bind specifically to the CAS gene DNA, the isolated P1-clone contains at least part of the human CAS gene.

Figure 10:
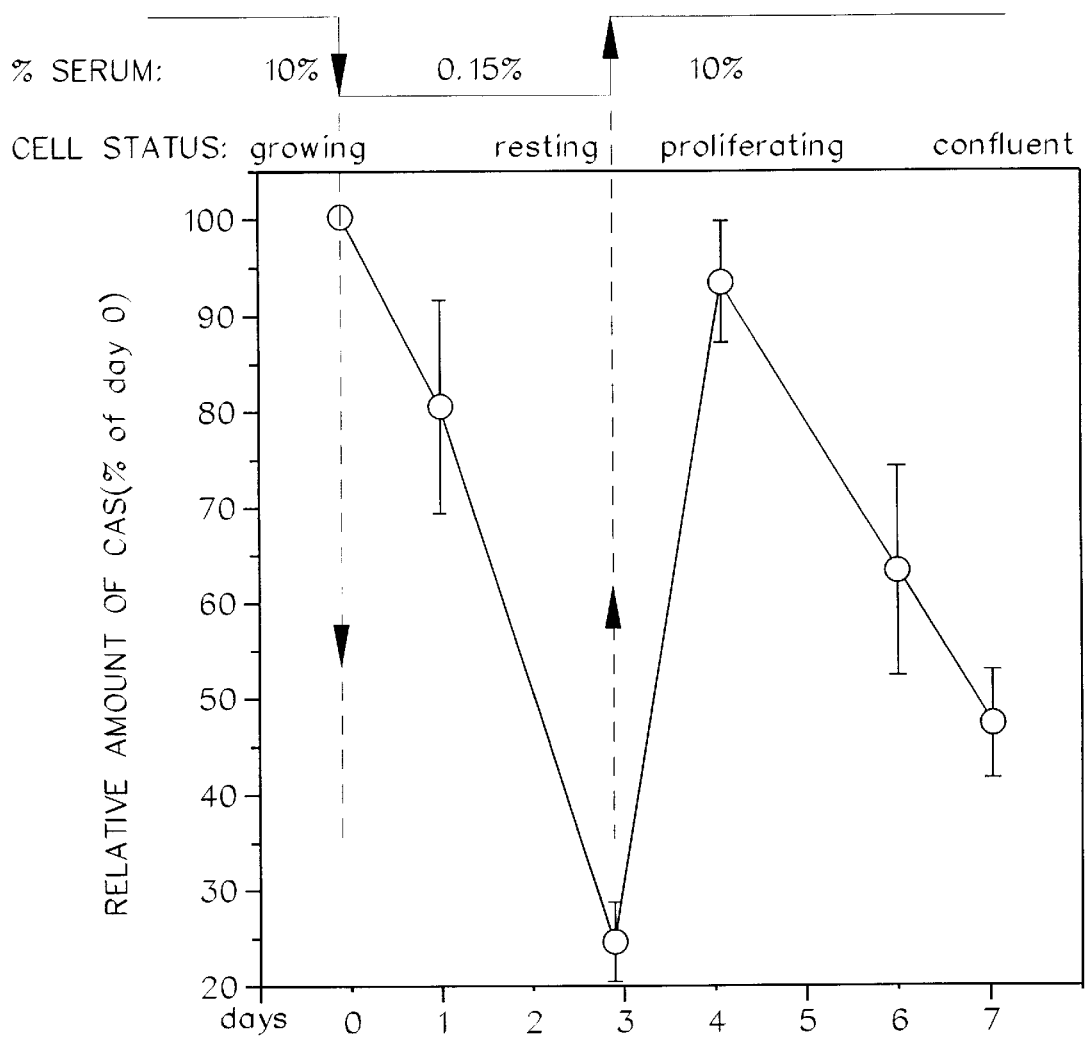
FIG. 10 shows a hypothetical, schematic organization of typical eukaryotic gene to represent the CAS gene and depict PCR amplification of genomic CAS DNA using the combinations of primers represented by the numbers 51+52 and 31+32.

The presence of the full length CAS gene in this P1 CAS clone was confirmed by PCR analysis of P1/hCAS using the primer pair P51 comprising 5'TGTGAAGCCGATC-GAGTGGC 3' (SEQ ID NO:7) and P52 comprising 5'TTCAGGGACATCCTGAAAGT 3' (SEQ ID NO:8) which amplify a 5'-end fragment from human CAS cDNA and P31 comprising 5'CCCCACTGATGGACACTGA 3' (SEQ ID NO:9) and P32 comprising 5' CTCACCAT-TGATGGAACCC 3' (SEQ ID NO:10) which amplify a 3'-end fragment from CAS cDNA (see FIG. 10 for a diagrammatic representation of these primers and their location on a hypothetical CAS gene). The rationale of using these primers and PCR analysis of P1/hCAS to confirm the completeness of the gene is depicted in FIG. 10 which is a schematic diagram of the organization of typical eukaryotic genes and does not represent the actual arrangement of introns and exons in the CAS gene. P51 and P52 will amplify a DNA fragment from P1/hCAS only if the 5'-end of the gene is present. Similarly, P31 and P32 will only result in a PCR fragment if the gene portion containing the 3'-end of the CAS coding region is present. FIG. 10 shows these combinations of primers as bars above the box labelled "CAS mRNA (cDNA)".

Using this approach, a specific DNA fragment was obtained with the P51 and P521 primer combination in a PCR reaction when the P1/hCAS was used as the PCR template but not when the template was not included in the reaction. The DNA amplified using this combination of P51 and P52 primers was about 2000 bp long. This 3'-end was also present on the P1/hCAS clone because when the combination of primers P31 and P32 were used with the P1/hCAS clone as template a similar fragment was amplified by PCR, whereas no fragments was observed without the P1/hCAS template.

A comparison of the fragment sizes obtained from this (3'-end) PCR with the distance of the primers in the CAS cDNA indicated that the 3'-end fragment is significantly larger than the distance on the cDNA. Thus, it is likely that an intron is present in between these primer positions in the human CAS gene.

EXAMPLE 12

PCR Detection of CAS Genomic DNA

Cancer cells often contain genetic abnormalities relative to normal cells that can be detected at the genomic level. To detect such genetic abnormalities associated with deletions, translocations or amplification of the 20q13 region, a PCR-based assay using primers specific for the CAS gene sequence is used.

Using the P51 and P52 combination of primers (P51/P52), genomic DNA from tissue suspected of having cancerous cells is amplified by PCR for a limited number of cycles. Similarly, the same source of genomic DNA is used as a template in a PCR reaction using the P31 and P32 combination (P31/P32) of primers (see also Example 11). As a control, genomic DNA from normal human tissue is similarly amplified in an independent reaction. The amplified DNA is then separated by gel electrophoresis, stained with a DNA intercalating dye, and the relative amount of DNA in each sample is determined by the degree of fluorescence of the amplified DNA under UV light. The amount of fluorescence in the amplification product from normal genomic DNA serves as a baseline control representing unamplified CAS sequences. In tissue in which the DNA containing the CAS gene is deleted (e.g., on one of the two chromosomes 20), a lesser amount of amplified CAS DNA is detected. In tissue in which the DNA conatining CAS gene is amplified a greater amount of amplified CAS DNA is detected. In tissue in which the CAS gene has been translocated to another location, a lesser (or no) CAS gene amplification may be detected depending on the location of the translocation breakpoint, or fragments of different lengths may be obtained following PCR amplification.

For performing this PCR-based assay, the following methods are used. Genomic DNA is purified from human tissues suspected of containing cancerous cells and from normal tissue as a control using standard purification methods. All PCR reactions are done in a final volume of 50 μl containing 250 ng of genomic DNA, 25 pmol of each primer (either the P31/P32 or the P51/P52 combination), 50 mM KCl, 10 mM Tris-HCl (pH 8.8), 1.5 mM MgCl$_2$, 0.1% Triton X-100, 200 μM of each dNTP and 2.5 units of Taql DNA polymerase. Amplification is for 15 cycles each consisting of 5 sec at 92° C., 1 min at 65° C. and 4 min at 72° C. followed by a single cycle of 12 min at 72° C. After amplification, 20 μl of each reaction is applied to an agarose gel for electrophoretic separation and staining using standard methods (Sambrook, J., et al., *Molecular cloning. A Laboratory Manual.*, 2nd ed., 1988).

Using this procedure, DNA isolated from tissue taken from a breast tumor is examined and found to contain more CAS genetic material compared to DNA from normal breast tissue for both the P31/P32 and P51/P52 combinations of primers. Thus, amplification of the CAS gene is detected in the tumor tissue.

It will be appreciated by those skilled in the art that a kit including the P31/P32 and/or P51/P52 combinations of primers or other primers specific for PCR amplification of CAS gene sequences could be used to detect genetic amplification of the CAS sequence. Determination of appropriate combinations of primers is well known in the art and is easily done using the sequence provided in SEQ ID NO:1. Such PCR-based kits are useful for detection in vitro or in vivo of cancer cells in human tissues. In addition to the CAS-specific primers, such a PCR kit may include primers specific for other areas of the genome (particularly for Chromosome 20 sequences), reagents used in performing the PCR (including but not limited to water, salts, buffers, dNTP solutions, Tagl DNA polymerase or other heat-resistant DNA polymerases). The amplified DNA sequence could be detected by separation and visualization of the products using gel electrophoresis or by other methods well known to those skilled in the art including DNA hybridization, filter binding and other well known techniques for specifically detecting specific DNA molecules.

Furthermore, it will be appreciated by those skilled in the art that a PCR-based kit may also be used to detect increased expression of the CAS gene. For example, a kit that includes a primer for transcribing CAS mRNA into cDNA by use of a reverse transcriptase (or other enzymes capable of producing cDNA) and primer combinations for then PCR amplifying the cDNA so produced would detect increased CAS gene expression. The amplified DNA may be detected using any of the procedures discussed above or other DNA detection methods well known in the art.

Thus, kits for detection of CAS genetic material or expression of CAS genes would include the PCR primer combinations needed for amplification and one or more reagents for performing PCR. A PCR kit may also reagents for detecting the amplified DNA.

EXAMPLE 13

Production of Antibodies that Specifically Recognize CAS Protein

To raise antibodies against the human CAS protein, we constructed plasmids for expression of fragments of CAS protein as recombinant His-tagged proteins in *E. coli* containing either amino acids 1–284 or 327–669 of CAS (Scherf, U. et al., *Proc. Natl. Acad. Sci. USA* 92:2670–2674, 1996).

Construction of Plasmids. DNA fragments encoding N-terminal or internal sequences of CAS were obtained by PCR using CAS cDNA as template. The primers 5'-GAGATCCTATA<u>CATATG</u>GAACTCCAGCGATG-3' (SEQ ID NO:11) with ATG translation initiation codon as part of a Nde 1 site (underlined), and 5'-TATCGCTG<u>GAATTC</u>TCATCCTAC-3'(SEQ ID NO:12) with an EcoRl site (underlined) for fusion to a hexahistidine tag were used to amplify the sequence for the first 284 aa. For the internal CAS fragment (aa 327–669) we used the primer 5'-CAGTTTGT<u>CATATG</u>CCTCATTATAAAATC-3'(SEQ ID NO:13) and 5'GAAGCAAA<u>GAATTC</u>ACTTGAAAGACGTATG-3' (SEQ ID NO:14). Nde I (start codon) and EcoRI (His$_6$) sites are underlined. PCR products were cloned into pCR II (invitrogen, San Diego, Calif.). The inserts were isolated from these vectors as Nde I/EcoRI fragments and cloned into pET-23b(+) (Novagen). The resulting plasmids, pUS6 for expression of CAS$_{1-284}$ (clone C2.6) and pUS7 for CAS$_{327-669}$ (clone C46) were confirmed to be correct by DNA sequencing.

Expression and Purification of CAS Protein Fragments. Recombinant CAS fragments were produced in *E. coli* cells containing these plasmids and purified from solubilized inclusion bodies by Ni-affinity chromatography (on Quiagen Ni-Chelation resin). The expression plasmids pUS6 and pUS7 were transformed into *Escherichia coli* BL21 (λDE3), expression induced at OD$_{600}$ of 2 with 2 mM isopropyl β-D-thiogalactoside, and the cells were harvested 2 h later. Both recombinant proteins accumulated in cytoplasmic inclusion bodies (IB), which were purified without preparation of spheroplasts prior to IB preparation. The IB were solubilized in 6 M GuHCl/0.1 M sodium phosphate/0.01 M tris-HCl, pH 8.0/5 mM 2-mercaptoethanol, and 10 mg was loaded onto a Ni-NTA column (Qiagen). The column was washed with 50 ml of wash buffer 8 M urea/0.1 M sodium phosphate/0.01 M Tris-HCl/5 mM 2-mercaptoethanol) at pH 8.0, 20 ml of wash buffer at pH 6.3, and 20 ml of wash buffer at pH 5.9. The proteins were eluted with wash buffer at pH 4.5. Protein concentration was determined with Branford assay reagent (Pierce) using bovine serum albumin (BSA) as a standard. After separation by SDS gel electrophoresis and Coomassie blue staining, only a single band of purified protein was detected for each of the clones corresponding to amino acids 1–284 or 327–669 of the CAS protein.

Immunizations. Rabbits were immunized with these purified proteins and polyclonal antibodies were produced that detected CAS protein on Western blots of total cell extracts from MCF-7 cells and W138 cells or from *E. coli* cells containing the recombinant CAS fragments. Each purified CAS protein fragment was diluted in phosphate-buffered saline (PBS), pH 7.4/1.5% Tween 20 (100 μg/ml or 180 μg/ml). Samples (250 μl) were diluted with 250 μl of Freund's adjuvant and 125 μl each was injected subcutaneously into four different sites of each HM(NZW)FBR rabbit [Hare-Marland, Hewitt, N.J.). Two rabbits were injected with each protein. Injection on day 1 was with complete Freund's adjuvant, the booster injections on days 14 and 28 were with incomplete adjuvant. Test bleeds were obtained 7 days after each injection and in 2-week intervals after the last injection.

Antibody Purification. Antibodies from rabbit R2.6-I against the N-terminal portion (CAS$_{1-284}$) and from rabbit R46-I against the center portion (CAS$_{327-669}$) of CAS were purified with immobilized protein A (Pierce). Anti-CAS$_{327-669}$ was further purified by affinity chromatography by Ni-NTA chromatography as described for preparation of immunogen but used 1M GuHCl without 2-mercaptoethanol (pH 4.5) as elution buffer. Fractions containing pure CAS protein were concentrated by Centricon 30 (Amicon) to 1.4 mg/ml, and 6 mg of the protein was then coupled to Affi-Gel 10 (Bio-Rad) activated with 0.1 sodium acetate, pH 4.5/1M GuHCl. Protein A purified anti-CAS$_{327-669}$ antibody from rabbit R46-1 dialyzed against 0.1M borate, pH 8.0/0.5 M NaCl was applied to the column equilibrated with dialysis buffer. After washing with dialysis buffer and 0.1M sodium acetate, pH 4.8/0.5 M NaCl, the antibody was eluted in 1-ml steps with 0.2 M sodium-acetate (pH 2.5) and neutralized with 500 µl of 1M Tris-HCl (pH 9.0). BSA was added to a final concentration of 1 mg/ml. Antibody fractions (≈35 µg of affinity-purified antibody per ml of immune serum) were dialyzed against PBS (pH 7.4) and stored at −20° C. The proteins were purified to near homogeneity (>95% pure). About 6 mg of purified recombinant protein was obtained from a 1-liter culture of E. coli expressing the N-terminal CAS$_{1-284}$ fragment and 11 mg of the CAS$_{327-669}$ fragment per liter was obtained.

Western Blot Analysis, Immunofluorescence, and Immunohistochemical Staining. Western blot analysis was performed with the Vectastain ABC kit (Vector Laboratories) using biotinylated anti-rabbit IgG (H+L) as secondary antibody, avidin horseradish peroxidase, and 3,3'-diaminobenzidine (DAB) for color development. In all cases, only a single band was detected using anti-CAS antibodies produced against the CAS amino acids 1–284 when the serum was diluted either 1:000 or 1:2000 in appropriate buffer. Control Western blots using the same amount of antigen and serum from pre-immunization rabbits at a 1:1000 dilution showed no detectable CAS band. Anti-CAS antibodies against CAS amino acids 327–669 showed a single band of detected protein on a Western blot when the serum was used at a 1:1000 dilution, and a weak band was detected when the serum was used at a 1:2000 dilution. The yield of affinity-purified anti-CAS$_{327-669}$ was ≈1.5% of the total protein A-purified antibodies. Affinity purified anti-CAS$_{327-669}$ specially detects ≦0.8 ng of CAS in Western blots developed with horseradish peroxidase and DAB as color substrate. A clear band was visible with 0.8 ng of purified recombinant CAS and 0.3 ng still showed a very weak band (data not shown). Control serum (at a dilution of 1:1000 or 1:2000) from the same rabbit before immunization showed no detectable signal on the Western blot.

When affinity purified anti-CAS antibodies against CAS amino acids 327–669 were used at 1:2000 dilution on a Western blot, a strong single band of CAS protein was detected showing that the purification concentrated the antibodies relative to the serum which barely detected CAS when diluted 1:2000. The affinity purified anti-CAS antibodies were used for immunohistological analysis of CAS expression in cells and tumors and for fluorescence activated cell sorter (FACS) analyses presented below.

EXAMPLE 14

Anti-CAS Antibodies can Distinguish Resting (Normal) Cells from Proliferating and Tumor Cells Because we have shown that CAS mRNA is highly expressed in proliferating cells and tumor cell lines, it is feasible to assume, that also the CAS protein should be present at high levels in proliferating and tumor cells and at low levels in normal cells (with few exceptions, e.g. testis). Because of that, the detection of relative amounts of CAS protein can be of value for tumor diagnosis, e.g. to distinguish tumor tissues from normal tissues.

Figure 11:
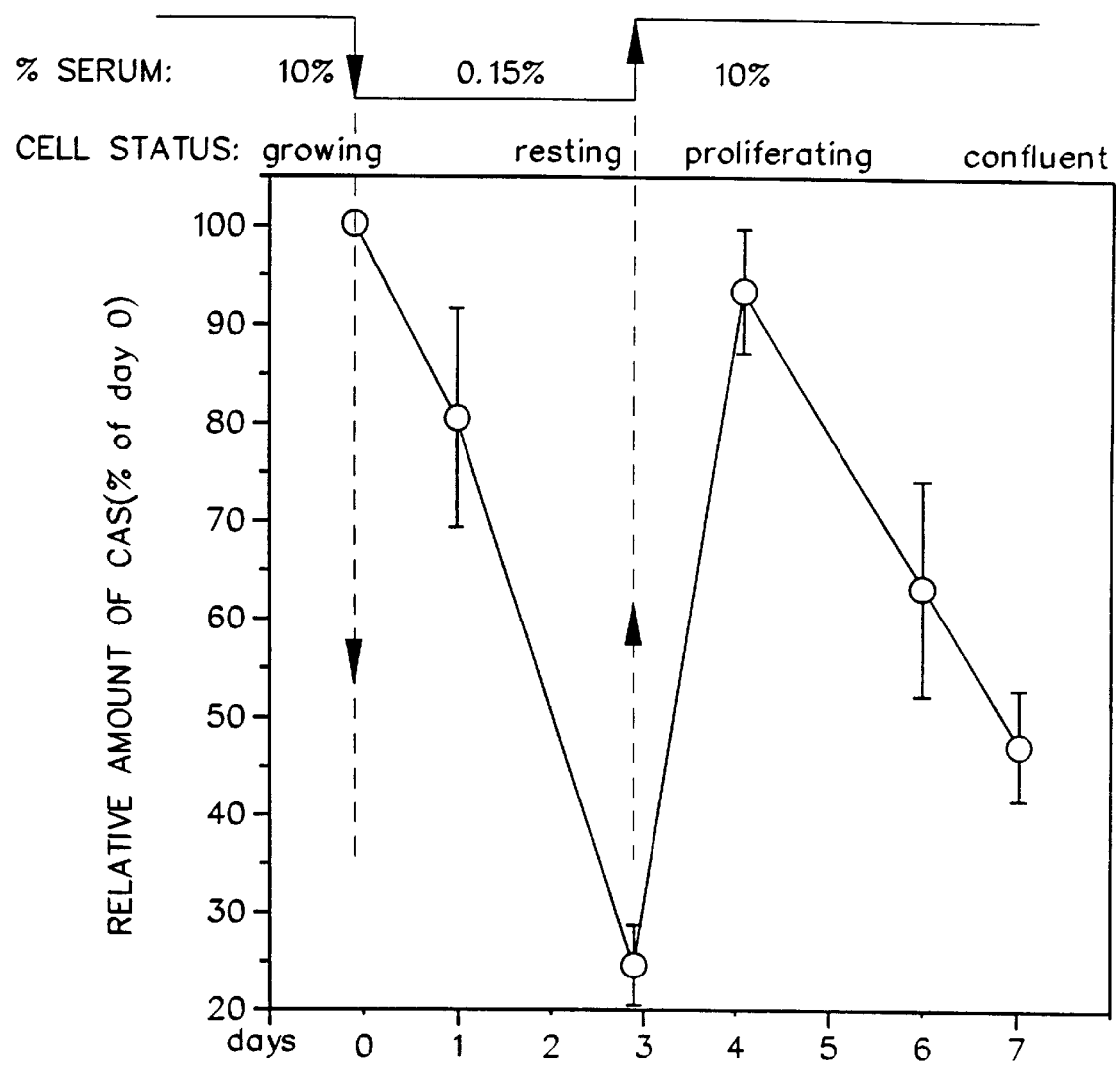
FIG. 11 shows the relative amount of CAS protein detected in growing and resting human WI-38 fibroblasts.

To demonstrate that the CAS protein level in cells is dependant on their proliferation status, we analyzed the CAS content in total cell extracts of resting human WI-38 fibroblasts (maintained in medium containing minimal serum) and of actively growing WI-38 cells (grown in medium containing 10–15%) serum). Serum starvation leads to cell growth arrest. Actively growing WI-38 fibroblasts (in 10% serum containing medium) were shifted to 0.15% serum containing medium for 3 days. The cells were then returned to 10% serum containing medium, in which cells resumed proliferation until they reached confluency, when growth was again arrested. Protein samples were obtained from the cells under the different growth conditions and analyzed by immunoblot with polyclonal rabbit anti-CAS antibodies (see Example 13). The CAS protein was detected as a single protein band of about 100 kDa by Western blotting of total cellular protein using anti-CAS antibodies. FIG. 11 shows that CAS was expressed at a higher level in growing cells and at significantly lower levels in resting cells. Furthermore, the amount of CAS protein increased when the resting cells were induced to proliferate by addition of serum. Thus, detection of elevated CAS expression in cells is indicative of cell proliferation.

To analyze whether CAS protein levels are elevated in growing cancer cells relative to normal cells, we compared the CAS protein content in total cell extracts of human WI-38 fibroblasts (resting and actively growing, see above) with the CAS content in MCF-7 breast cancer cells, again using Western blots with anti-CAS antibodies. We found that CAS was expressed at a significantly higher level in the cancer cells compared to the "normal" cells, independent of whether the normal cells were growing or resting.

The high levels of CAS protein in cancer cells can also be detected using CAS-specific antibodies and secondary antibodies with fluorescent tags and immunofluorescence techniques well known to those skilled in the art. The presence of CAS protein in various cancer cells was detected by standard immunofluorescence and microscopic examination of MCF-7 breast cancer and A431 epidermoid cells. FACS analysis was used to detect CAS protein in CA46 lymphoma cells. When cells were stained with anti-CAS fluorescently labeled antibodies, the cells exhibited an average relative fluorescence about 100-fold greater than that of cells that were not stained with anti-CAS fluorescently labeled antibodies. In this FACS analysis, the relative fluorescence resulting from binding of the fluorescently-labeled anti-CAS antibody (on the Y axis) was graphed as a function of the DNA content of the cells determined by propidium iodite staining (on the X axis).

It will be appreciated by those skilled in the art that a kit for diagnosing cancer can be based on anti-CAS antibodies such as those described above. An antibody based diagnostic kit could use the anti-CAS antibodies in a variety of ways to detect cellular CAS protein in cancer cells. A kit could be used to detect binding of anti-CAS antibodies to CAS protein by directly measuring fluorescence from anti-CAS antibodies directly labeled with a fluorescent marking in a fluorescence immunoassay using techniques well known to those skilled in the art. Alternatively, a kit could rely on other ways of detecting binding of anti-CAS antibody to CAS protein including detection of fluorescence using a fluorescently-labeled secondary antibody to bind to the anti-CAS antibody (based on specific binding to the anti-CAS antibody or cross-species antibody binding, dependent on either the variable or constant regions of the anti-CAS antibody, respectively). It will be appreciated by those skilled in the art that radiolabeling of the anti-CAS antibody or the secondary antibody that binds to the anti-CAS antibody could be effectively substituted for fluorescent labeling and the kit would rely on a radioimmunoassay (RIA). Furthermore, an enzyme substrate attached to the anti-CAS antibody or the secondary antibody that binds to the anti-CAS antibody could be used to detect binding by measuring the relative enzymatic activity of the bound antibodies in a enzyme linked immunosorbent assay (ELISA) using reactions well known to those skilled in the art. Those skilled in the art will further appreciate that an antibody-based kit could use latex beads, either directly linked to the anti-CAS antibody or linked to the secondary antibody that binds to the anti-CAS antibody. Anti-CAS antibodies could further be used in a kit in which the anti-CAS antibodies serve as part of a sandwich immunoassay in which the CAS protein is immobilized to a solid support for detection. It will be understood that these examples are nonlimiting and additional methods of antibody-based detection of CAS protein are also contemplated for use in a kit of the present invention.

We conclude that elevated CAS expression in cells is indicative for cell proliferation, and that higher levels of CAS protein are detectable in cancer cells, compared to most normal cells.

EXAMPLE 15

Localization of CAS Protein in Cellular Microtubules and Metaphase Spindles

Using immuno-assays, the CAS protein was localized to the cytoplasmic fraction of cells, primarily in microtubules and in mitotic spindles of metaphase cells. Western blot assays were done essentially as described in Example 13. For immunofluorescence, affinity-purified anti-CAS preparation (10 μg/ml) or antitubulin monoclonal antibody (10 μg/ml) (clone YL ½-supernatant; Accurate Scientific, Westbury, N.Y.) were incubated with MCF-7, A431, OVCAR3, or KB cells grown for 1 day in 35-mm dishes to subconfluency. Cells were fixed and permeabilized using 3.7% formaldehyde in PBS for 10 min followed by inclusion of 0.1% saponin in all subsequent incubations. Bound antibody was detected with goat anti-rat IgG rhodamine for anti-tubulin antibody and with goat anti-rabbit-rhodamine for anti-CAS antibody. For double-label immunofluorescence, MCF-7 cells were fixed and processed as descried for single-label immunofluorescence. Cells were then sequentially incubated with rabbit anti-CAS and rat monoclonal anti-tubulin, followed by affinity-purified goat anti-rabbit rhodamine having minimal cross-reaction to rat, and goat anti-rat fluorescein having minimal cross-reaction to rabbit (Jackson ImmunoResearch). Controls demonstrated that the two antibody systems showed no cross-reactivity and no cross-detection between fluorescence channels. Frozen tissue samples from the Hollings Cancer Center Tumor Bank Collection at the Medical University of South Carolina were cryostat sectioned and processed for immunohistochemical staining.

Cell Fractionation and Preparation of Cytoskeleton. MCF-7 or A431 cells ($2\times10^6$) were chilled to 4° C., washed three times with ice-cold Dulbecco's PBS without $CA^{2+}/Mg^{2+}$, scraped from the flasks, and suspended in 1 ml of hypotonic buffer (25 mM Tris-HCl, pH 7.4/2 mM $MgCl_2$/1 mM EDTA) for 15 min on ice. Then the suspension was homogenized (20 strokes in a Dounce homogenizer) and centrifuged (1,000×g at 4° C. for 5 min). The pellet is the nuclear fraction. The supernatant was centrifuged (100,000×g at 4° C. for 60 min.) and the supernatant from this configuration step is the cytosolic fraction. The pellet from the second centrifugation step, which contains mainly membranes, was resuspended in hypotonic buffer. Cytoskeletons of MCF-7 cells grown in 35-mm poly(L-lysine) dishes were prepared by washing cells attached to the dishes three times with 0.1M Mes/1 mM EGTA/1 mM $MgCl_2$/4% PEG 8000, pH 6.5, followed by incubation for 20 min with 0.2% Triton X-100 in the same buffer, and washing three times with PBS. The cytoskeletons still attached to the dishes were fixed with 3.7% formaldehyde for 10 min, washed three times with PBS, and subjected to immunofluorescence.

CAS is an abundant cytoselic protein. CAS cDNA contains an open reading frame encoding a protein of about 100-kDa. To analyze the specificity of the antibody preparation and to confirm the open reading frame deduced from CAS cDNA, we analyzed total cell extracts of MCF-7 and A431 cells by Western blots. We detected an approximately 100-kDa band in the extracts with immune serum but not with preimmune serum. Using immunoblot analyses of total cell protein of MCF-7 cells on 4–15% SDS gels with anti-$CAS_{1-284}$ and anti-$CAS_{327-669}$ antibodies, we found that both anti-CAS antisera specifically detected an approximately 100-kDa protein, as predicted from the cDNA sequence, while the corresponding preimmune sera did not.

To evaluate the cellular localization of CAS protein, we homogenized MCF-7 and A431 cells and prepared fractions containing membranes, cytosol, and nuclei. Western blot analysis with anti-$CAS_{1-284}$ and anti-$CAS_{327-669}$ antibodies showed that CAS is present exclusively in the cytosolic fraction.

To obtain an estimate of the number of CAS molecules per cell, we compared the CAS signal intensity in the cytosolic fraction of MCF-7 cells with the signal intensity of known amounts of recombinant CAS. We found that the signal from protein present in $10^4$ cells corresponded to about 1 ng of CAS. Thus, one MCF-7 cell contains about 0.1 pg of CAS (i.e., $\approx10^{-18}$ mol or $\approx600,000$ molecules), indicating that CAS is an abundant protein. Taking into account the variations between different immunoblot analyses and extract preparations, we estimate the number of CAS molecules is between $2\times10^5$ and $1\times10^6$ per cell in actively growing cells.

CAS is associated with microtubules. To obtain information about the intracellular distribution of CAS, we analyzed permeabilized MCF-7, A431, OVCAR3, and KB cells by immunofluorescence with affinity-purified anti-$CAS_{327-669}$ antibody. Anti-CAS antibody shows a diffuse background staining and clear staining of structures that form an intracellular network in all cell lines. This distribution resembles that of microtubules. We therefore compared cells stained with anti-CAS antibody to cells stained with anti-tubulin antibody and found that CAS is distributed in cells in a pattern similar to tubulin, indicating that CAS is associated with or part of microtubules. Anti-CAS staining of metaphase MCF-7 cells showed that CAS is also associated with the chromosome segregation spindle in mitotic cells. The spindle and the intercellular bridge between cells that have just divided stained strongly. The intracellular distribution of CAS, as defined with anti-$CAS_{327-669}$ antibody, was confirmed with protein A-purified anti-$CAS_{1-234}$ antibody, which showed the same intracellular CAS distribution and localization. Also, a separate double-label immunofluorescence experiment was performed which demonstrated that the tubular structures detected by anti-CAS and anti-tubulin antibodies are the same.

CAS is not an integral part of the microtubules and is not tightly bound to microtubules. Possible explanation for a tubulin-like intracellular distribution of CAS, as observed by immunofluorescence with anti-CAS antibody, are that (1) the polyclonal antibody preparations crossreact with tubulin, (2) CAS is an integral part of microtubules, or (3) CAS is associated with but not part of microtubules. To rule out the possibility that our antibody preparations cross-react with tubulin, we analyzed by Western blot analysis a tubulin preparation (T-4925; Sigma) derived from bovine brain, which contains about 15% microtubule-associated proteins (MAP). The gel was loaded with 60 μg of tubulin, and no reactivity of anti-CAS with tubulin was detected. Also, anti-CAS$_{327-669}$ antibody did not react with tubulin-associated proteins in immunoblots. Although our antibodies were prepared against human CAS, we would expect to detect bovine CAS, because the cDNA sequence is highly conserved between humans and yeast, and our antibody detected mouse CAS. Thus, our antibody preparations do not cross-react with tubulin or with MAP that are present in this tubulin preparation. Furthermore, sera from animals that were independently immunized with different parts of CAS showed the same distribution pattern and the same protein size, making it unlikely that the signals observed were due to cross-reactivity. Thus, CAS is either an integral part of microtubules or is associated with microtubules.

To distinguish between these possibilities, we chose two approaches. First, we isolated cytoskeletal microtubules by an EGTA/Mg$^{2+}$/Triton X-100 method, which retains the microtubule network but removes loosely associated proteins. If CAS is an integral part of microtubules or very tightly bound to microtubules, the cytoskeletal preparation should stain with anti-CAS and with anti-tubulin antibodies. If CAS is associated loosely to microtubules, the anti-CAS staining pattern should be weaker than with anti-tubulin anti-tubulin. Our immunofluorescent results showed cytoskeletal preparations of MCF-7 cells stained with anti-CAS$_{327-669}$ and anti-tubulin antibodies but the distribution of CAS and tubulin was different. That is, anti-tubulin strongly stained the microtubule structures but anti-CAS produced a weak diffuse image. Only highly stable structures such as intercellular bridges still showed some anti-CAS staining. These results indicate that although CAS is associated with the microtubular cytoskeleton, as seen by whole cell staining, it is not an integral part of the cytoskeleton because most of the CAS protein was removed from the cytoskeleton during the EGTA/Triton X-100 preparation.

We also analyzed CAS distribution in MCF-7 cells that were treated with vincristine or taxol. Vincristine treatment results in formation of tubulin paracrystals and taxol produces tubulin bundles. If CAS were an integral part of microtubules, we would expect similar images of vincristine- and texol-treated cells stained with anti-tubulin or anti-CAS. However, we found that anti-CAS produced a strong diffuse cytoplasmic staining and only a weak immunofluorescence signal associated with paracrystals and bundles, in contrast to strong anti-tubulin staining of paracrystals and microtubule bundles in vincristine- and taxol-treated cells. Thus, CAS is associated with but not an integral part of microtubules and CAS that is bound to microtubules is released by the EGTA/Triton X-100 incubation during cytoskeleton preparation and in vincristine- and taxol-treated cells.

EXAMPLE 16

Localization of CAS Protein in Lymphoid Neoplasms

Because CAS expression is associated with cell proliferation and apoptosis, factors known to play a role in lymphoma development, and CAS is highly expressed in some leukemia and lymphoma cell lines (e.g., HL-60, K-562, MOLT-4 and Raji), the role of CAS expression in lymphoma development was investigated. CAS protein distribution in normal tonsils and different lymphoma subtypes was analyzed by immunohistochemistry using antibodies against CAS (as described in Examples 13–15).

Formalin or B5 fixed and paraffin embedded biopsies from 26 cases of malignant lymphomas were selected from the histopathology files of the Hematopathology Section, Laboratory of Pathology, National Cancer Institute, National Institutes of Health (Bethesda, Md. USA). The lymphomas were classified according to the Revised European-American Classification of Lymphoid Neoplasms (REAL; Harris, N. L. et al., Blood 1:1361–1392, 1994). The cases included five follicular lymphomas (FL), four B-cell chronic lymphoid leukemias (B-CLL), six diffuse large B-cell lymphomas (DLBCL), two peripheral and three precursor (lymphoblastic) T-cell lymphomas (TCL), four anaplastic large cell lymphomas of T- and null-cell phenotypes (ALCL), and two cases of Hodgkin's disease (HD). All cases had been immunophenotyped either in paraffin or frozen sections.

Polyclonal antibodies against CAS were raised immunized with recombinant CAS protein and purified essentially as described in Example 13.

Five μm paraffin sections were mounted on Fisherbrand/Plus Superfrost slides (Fisher Scientific, Pittsburg, Pa.). After blocking endogenous peroxidase activity, a wet heat antigen retrieval was performed by boiling in a microwave pressure cooker (Nordic Ware, Minneapolis, Minn.) in 0.01M citrate buffer, pH 6.0, at 800 W for 40 min. The sections were rinsed in 0.05 M Tris-HCL saline, pH 7.6 (TBS) containing 5% fetal calf serum (FCS) for 15 min. Then sections were incubated overnight with anti-CAS antibody (0.1 μg/ml in TBS containing 20% FCS and 0.1% NaN$_3$) at room temperature (RT). Biotinylated anti-rabbit anti-mouse secondary antibody was used for detection of anti-CAS binding, and the peroxidase reaction was developed using well known techniques (e.g., as utilized in the StreptABComples/HRP Duet Kit and DAKO AEC Substrate System, DAKO Corporation, Carpinteria, Calif.). For simultaneous staining of CAS and Ki-67 proteins, biotinylated goat anti-rabbit immunoglobulins secondary antibody (⅟400 dilution) and streptavidin-peroxidase conjugate (⅟600 dilution) were used for the CAS immunoreaction (both reagents from DAKO). After the development of the peroxidase reaction, the sections were incubated for 60 min at RT with a mouse anti-Ki-67-monoclonal antibody (M1B1) at ⅟10 dilution; Immunotech, Westbrook, Me.) and then goat anti-mouse immunoglobulin (⅟25 dilution) and a mouse APAAP complex (⅟50 dilution; both reagents from DAKO) were applied. The second immunoreaction was visualized with BCIP/NBT (Boehringer Mannheim). All sections were counterstained with hematoxylin and mounted with Glycergel™ (DAKO). Immunohistochemical staining with anti-CAS antibody of fixed and paraffin-embedded specimens compared to staining of frozen tissue slides revealed similar staining patterns for both specimen types. Therefore, all further experiments were done on formalin-fixed, paraffin embedded tissue.

Normal tonsils stained with anti-CAS antibody and double stained with anti-CAS/Ki-67 antibodies showed a polarized CAS staining of about 20% of the cells, condensed to the dark zone of the follicle. The strongest staining was found in the large cells. In contrast, the majority of mantle zone and interfollicular cells did not stain for CAS, except for some single larger cells having moderate to strong staining. The staining was confined to the cytoplasm of the positive cells. Anti-CAS/anti-Ki-67 double staining demonstrated that most of the strongly CAS-positive cells were also positive for Ki-67 but about 10% to 15% of the strongly CAS-positive cells did not stain for Ki-67. Furthermore, almost all weakly CAS-positive cells were negative for Ki-67.

Expression and distribution of CAS was analyzed in 26 lymphomas (see Table 3). Staining of CAS protein in follicular lymphomas demonstrated a very intense cytoplasmatic reaction in 50% to 60% of the atypical larger cells. Compared to the distribution of CAS-positive cells in normal tonsils, these strongly CAS-positive lymphoma cells were stained in a more scattered and irregular pattern throughout the tumor, although most of the CAS-positive cells were confined to the follicles but not in a polarized manner. Anti-CAS/anti-Ki-67 double staining showed a good correlation between CAS and Ki=67 expression but about 10% more CAS-positive cells were detected compared to Ki-67 positive cells. The small cells of the follicles were CAS-negative or showed weaker staining.

In histologically aggressive lymphomas (e.g., ALCL and DLBCL), we found that 70% of the multinucleated large tumor cells were CAS-positive. Most of these cells were also positive for Ki67, but about 10% of the CAS-positive cells were negative for Ki-67. In addition to ALCL and DLBCL, we analyzed B-CLL, TCL and Hodgkin's disease lymphomas.

The results of immunostaining of the lymphoma specimens are summarized in Table 3. B-CLL showed a generally weaker staining with anti-CAS, staining about 5% to 10% of the malignant cells; anti-CAS/anti-Ki-67 doublestaining showed the same results. These weakly CAS-positive cells were scattered throughout the atypical infiltrate and are most likely paraimmunoblasts. In TCL, about 15% to 20% of the malignant cells were weakly CAS-positive, which reflected the staining pattern of Ki-67. The Hodgkin's disease cases revealed a strong staining for CAS and Ki-67 in 80% of the Reed-Sternberg and mononuclear variant cells.

The aggressive NHL and HD lymphomas displayed the strongest CAS-positive staining, with up to 80% of the malignant cells staining. The CAS and Ki-67 expression patterns are almost congruent within the different lymphoma subtypes, but a subpopulation of some malignant cells that were CAS-positive but Ki-67 negative was observed.

These results show that CAS protein is abundant in benign proliferating lymphocytes of the tonsilar follicles. CAS was predominantly in the larger malignant cells of the studied lymphoid tumors and thus may be used as a marker for diagnosis and prognosis testing of these types of lymphomas using similar antibody staining techniques as described above. The reagents for detecting CAS in suspected lymphoma tissue by immunofluorescent methods may be supplied in a kit for diagnostic use.

TABLE 3

CAS Staining in Normal Tonsils and Various Lymphomas

| Tissue | Number | % CAS-staining Cells | Tissue Distribution |
|---|---|---|---|
| Tonsil | 5 | 20 | polarized in dark zone of follicle |
| Follicular Lymphoma | 5 | 50–60 | scattered through neoplastic nodules |
| Diffuse Large B-cell & Anaplastic Large Cell Lymphomas | 10 | 60–70 | in multinucleated large cells |
| B-cell Chronic Lymphoid Leukemia | 4 | 5–10 | weak & scattered through infiltrate |
| T-cell Lymphoma | 5 | 15–20 | weak & scattered through infiltrate |
| Hodgkin's Disease | 2 | 80 | Reed-Sternberg & mononuclear variants |

What is claimed is:

1. A method of detecting human proliferating cells, comprising measuring a level of a human CAS protein in a human cell sample and detecting the human CAS protein at a level at least two-fold greater than a level of a human CAS protein in normal nonproliferating human cells.

2. The method of claim 1, wherein said human CAS protein is detected by binding of an antibody that specifically recognizes human CAS protein.

3. The method of claim 2, wherein the antibody binding is detected using immunofluorescence.

4. The method of claim 1, wherein human cell sample is obtained from breast, colon or lymph tissue.

5. The method of claim 1, wherein said human CAS protein is detected in about 5% to about 80% of cells in the human cell sample.

6. The method of claim 1, wherein said human CAS protein is detected in about greater than 20% of cells in the human cell sample.

7. The method of claim 1, wherein said human CAS protein is detected in about 50% to about 80% of cells in the human cell sample.

8. The method of claim 1, wherein the human cell sample comprises human cancerous cells and the normal nonproliferating human cells comprise noncancerous human cells.

9. The method of claim 1, wherein the human CAS protein is detected in a cytoplasmic fraction of the human cell sample.

10. The method of claim 1, wherein the human CAS protein is detected in a association with microtubules or mitotic spindles in the human cell sample.

11. An isolated antibody that specifically recognizes a human CAS protein.

12. The antibody according to claim 11, wherein the antibody is produced by immunization of a mammal with a human CAS protein consisting of amino acids 1 to 284 of SEQ ID NO:2.

13. The antibody according to claim 11, wherein the antibody is produced by immunization of a mammal with a human CAS protein consisting of amino acids 327 to 669 of SEQ ID NO:2.

14. A kit for diagnosing human cancer, said kit comprising an antibody according to claim 11 and a label for indicating binding of said antibody to human CAS protein.

* * * * *

SEQUENCE LISTING (1) GENERAL INFORMATION:

(iii) NUMBER OF SEQUENCES: 14

(2) INFORMATION FOR SEQ ID NO:1:

(i) SEQUENCE CHARACTERISTICS:
      (A) LENGTH: 3180 base pairs
      (B) TYPE: nucleic acid
      (C) STRANDEDNESS: single
      (D) TOPOLOGY: linear (ii) MOLECULE TYPE: cDNA (iii) HYPOTHETICAL: NO (iv) ANTISENSE: NO (v) FRAGMENT TYPE:

(vi) ORIGINAL SOURCE:

(xi) SEQUENCE DESCRIPTION: SEQ ID NO:1:

| | | | | | |
|---|---|---|---|---|---|
| GTCGCGCCAT | TTTGCCGGGG | TTTGAATGTG | AGGCGGAGCG | GCGGCAGGAG | CGGATAGTGC | 60 |
| CAGCTACGGT | CCGCGGCTGG | GGTTCCCTCC | TCCGTTTCTG | TATCCCCACG | AGATCCTATA | 120 |
| GCAATGGAAC | TCAGCGATGC | AAATCTGCAA | ACACTAACAG | AATATTTAAA | GAAAACACTT | 180 |
| GATCCTGATC | CTGCCATCCG | ACGTCCAGCT | GAGAAATTTC | TTGAATCTGT | TGAAGGAAAT | 240 |
| CAGAATTATC | CACTGTTGCT | TTTGACATTA | CTGGAGAAGT | CCCAGGATAA | TGTTATCAAA | 300 |
| GTATGTGCTT | CAGTAACATT | CAAAAACTAT | ATTAAAAGGA | ACTGGAGAAT | TGTTGAAGAT | 360 |
| GAACCAAACA | AAATTTGTGA | AGCCGATCGA | GTGGCCATTA | AAGCCAACAT | AGTGCACTTG | 420 |
| ATGCTTAGCA | GCCCAGAGCA | AATTCAGAAG | CAGTTAAGTG | ATGCAATTAG | CATTATTGGC | 480 |
| AGAGAAGATT | TTCCACAGAA | ATGGCCTGAC | TTGCTGACAG | AAATGGTGAA | TCGCTTTCAG | 540 |
| AGTGGAGATT | TCCATGTTAT | TAATGGAGTC | CTCCGTACAG | CACATTCATT | ATTTAAAAGA | 600 |
| TACCGTCATG | AATTTAAGTC | AAACGAGTTA | TGGACTGAAA | TTAAGCTTGT | TCTGGATGCC | 660 |
| TTTGCTTTGC | CTTTGACTAA | TCTTTTTAAG | GCCACTATTG | AACTCTGCAG | TACCCATGCA | 720 |
| AATGATGCCT | CTGCCCTGAG | GATTCTGTTT | TCTTCCCTGA | TCCTGATCTC | AAAATTGTTC | 780 |
| TATAGTTTAA | ACTTTCAGGA | TCTCCCTGAA | TTTTGGGAAG | GTAATATGGA | AACTTGGATG | 840 |
| AATAATTTCC | ATACTCTCTT | AACATTGGAT | AATAAGCTTT | TACAAACTGA | TGATGAAGAG | 900 |
| GAAGCCGGCT | TATTGGAGCT | CTTAAAATCC | CAGATTTGTG | ATAATGCCGC | ACTCTATGCA | 960 |
| CAAAAGTACG | ATGAAGAATT | CCAGCGATAC | CTGCCTCGTT | TTGTTACAGC | CATCTGGAAT | 1020 |
| TTACTAGTTA | CAACGGGTCA | AGAGGTTAAA | TATGATTTGT | TGGTAAGTAA | TGCAATTCAA | 1080 |
| TTTCTGGCTT | CAGTTTGTGA | GAGACCTCAT | TATAAGAATC | TATTTGAGGA | CCAGAACACG | 1140 |
| CTGACAAGTA | TCTGTGAAAA | GGTTATTGTG | CCTAACATGG | AATTTAGAGC | TGCTGATGAA | 1200 |
| GAAGCATTTG | AAGATAATTC | TGAGGAGTAC | ATAAGGAGAG | ATTTGGAAGG | ATCTGATATT | 1260 |
| GATACTAGAC | GCAGGGCTGC | TTGTGATCTG | GTACGAGGAT | TATGCAAGTT | TTTTGAGGGA | 1320 |
| CCTGTGACAG | GAATCTTCTC | TGGTTATGTT | AATTCCATGC | TGCAGGAATA | CGCAAAAAAT | 1380 |
| CCATCTGTCA | ACTGGAAACA | CAAAGATGCA | GCCATCTACC | TAGTGACATC | TTTGGCATCA | 1440 |
| AAAGCCCAAA | CACAGAAGCA | TGGAATTACA | CAAGCAAATG | AACTTGTAAA | CCTAACTGAG | 1500 |
| TTCTTTGTGA | ATCACATCCT | CCCTGATTTA | AAATCAGCTA | ATGTGAATGA | ATTTCCTGTC | 1560 |
| CTTAAAGCTG | ACGGTATCAA | ATATATTATG | ATTTTTAGAA | ATCAAGTGCC | AAAAGAACAT | 1620 |
| CTTTTAGTCT | CGATTCCTCT | CTTGATTAAT | CATCTTCAAG | CTGGAAGTAT | TGTTGTTCAT | 1680 |
| ACTTACGCAG | CTCATGCTCT | TGAACGGCTC | TTTACTATGC | GAGGGCCTAA | CAATGCCACT | 1740 |
| CTCTTTACAG | CTGCAGAAAT | CGCACCGTTT | GTTGAGATTC | TGCTAACAAA | CCTTTTCAAA | 1800 |
| GCTCTCACAC | TTCCTGGCTC | TTCAGAAAAT | GAATATATTA | TGAAAGCTAT | CATGAGAAGT | 1860 |
| TTTTCTCTCC | TACAAGAAGC | CATAATCCCC | TACATCCCTA | CTCTCATCAC | TCAGCTTACA | 1920 |
| CAGAAGCTAT | TAGCTGTTAG | TAAGAACCCA | AGCAAACCTC | ACTTTAATCA | CTACATGTTT | 1980 |
| GAAGCAATAT | GTTTATCCAT | AAGAATAACT | TGCAAAGCTA | ACCCTGCTGC | TGTTGTAAAT | 2040 |
| TTTGAGGAGG | CTTTGTTTTT | GGTGTTTACT | GAAATCTTAC | AAAATGATGT | GCAAGAATTT | 2100 |
| ATTCCATACG | TCTTTCAAGT | GATGTCTTTG | CTTCTGGAAA | CACACAAAAA | TGACATCCCG | 2160 |
| TCTTCCTATA | TGGCCTTATT | TCCTCATCTC | CTTCAGCCAG | TGCTTTGGGA | AGAACAGGA | 2220 |
| AATATTCCTG | CTCTAGTGAG | GCTTCTTCAA | GCATTCTTAG | AACGCGGTTC | AAACACAATA | 2280 |

```
GCAAGTGCTG CAGCTGACAA AATTCCTGGG TTACTAGGTG TCTTTCAGAA GCTGATTGCA    2340

TCCAAAGCAA ATGACCACCA AGGTTTTTAT CTTCTAAACA GTATAATAGA GCACATGCCT    2400

CCTGAATCAG TTGACCAATA TAGGAAACAA ATCTTCATTC TGCTATTCCA GAGACTTCAG    2460

AATTCCAAAA CAACCAAGTT TATCAAGAGT TTTTTAGTCT TTATTAATTT GTATTGCATA    2520

AAATATGGGG CACTAGCACT ACAAGAAATA TTTGATGGTA TACAACCAAA AATGTTTGGA    2580

ATGGTTTTGG AAAAAATTAT TATTCCTGAA ATTCAGAAGG TATCTGGAAA TGTAGAGAAA    2640

AAGATCTGTG CGGTTGGCAT AACCAACTTA CTAACAGAAT GTCCCCCAAT GATGGACACT    2700

GAGTATACCA AACTGTGGAC TCCATTATTA CAGTCTTTGA TTGGTCTTTT TGAGTTACCC    2760

GAAGATGATA CCATTCCTGA TGAGGAACAT TTTATTGACA TAGAAGATAC ACCAGGATAT    2820

CAGACTGCCT TCTCACAGTT GGCATTTGCT GGGAAAAAAG AGCATGATCC TGTAGGTCAA    2880

ATGGTGAATA ACCCCAAAAT TCACCTGGCA CAGTCACTTC ACATGTTGTC TACCGCCTGT    2940

CCAGGAAGGG TTCCATCAAT GGTGAGCACC AGCCTGAATG CAGAAGCGCT CCAGTATCTC    3000

CAAGGGTACC TTCAGGCAGC CAGTGTGACA CTGCTTTAAA CTGCATTTTT CTAATGGGCT    3060

AAACCCAGAT GGTTTCCTAG GAAATCACAG GCTTCTGAGC ACAGCTGCAT TAAAACAAAG    3120

GAAGTTTTCC TTTTGAACTT GTCACGAAAA AAAAAAAAAA AAAAAAAAAA AAAAAAAAA     3180
```

(2) INFORMATION FOR SEQ ID NO:2:

(i) SEQUENCE CHARACTERISTICS:
        (A) LENGTH: 971 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTISENSE: NO (v) FRAGMENT TYPE: N-terminal (vi) ORIGINAL SOURCE:

(xi) SEQUENCE DESCRIPTION: SEQ ID NO:2:

```
Met Glu Leu Ser Asp Ala Asn Leu Gln Thr Leu Thr Glu Tyr Leu Lys
  1               5                  10                  15

Lys Thr Leu Asp Pro Asp Pro Ala Ile Arg Arg Pro Ala Glu Lys Phe
             20                  25                  30

Leu Glu Ser Val Glu Gly Asn Gln Asn Tyr Pro Leu Leu Leu Leu Thr
         35                  40                  45

Leu Leu Glu Lys Ser Gln Asp Asn Val Ile Lys Val Cys Ala Ser Val
     50                  55                  60

Thr Phe Lys Asn Tyr Ile Lys Arg Asn Trp Arg Ile Val Glu Asp Glu
 65                  70                  75                  80

Pro Asn Lys Ile Cys Glu Ala Asp Arg Val Ala Ile Lys Ala Asn Ile
                 85                  90                  95

Val His Leu Met Leu Ser Ser Pro Glu Gln Ile Gln Lys Gln Leu Ser
            100                 105                 110

Asp Ala Ile Ser Ile Ile Gly Arg Glu Asp Phe Pro Gln Lys Trp Pro
        115                 120                 125

Asp Leu Leu Thr Glu Met Val Asn Arg Phe Gln Ser Gly Asp Phe His
    130                 135                 140
```

-continued

```
Val Ile Asn Gly Val Leu Arg Thr Ala His Ser Leu Phe Lys Arg Tyr
145                 150                 155                 160

Arg His Glu Phe Lys Ser Asn Glu Leu Trp Thr Glu Ile Lys Leu Val
                165                 170                 175

Leu Asp Ala Phe Ala Leu Pro Leu Thr Asn Leu Phe Lys Ala Thr Ile
            180                 185                 190

Glu Leu Cys Ser Thr His Ala Asn Asp Ala Ser Ala Leu Arg Ile Leu
        195                 200                 205

Phe Ser Ser Leu Ile Leu Ile Ser Lys Leu Phe Tyr Ser Leu Asn Phe
    210                 215                 220

Gln Asp Leu Pro Glu Phe Trp Glu Gly Asn Met Glu Thr Trp Met Asn
225                 230                 235                 240

Asn Phe His Thr Leu Leu Thr Leu Asp Asn Lys Leu Leu Gln Thr Asp
                245                 250                 255

Asp Glu Glu Glu Ala Gly Leu Leu Glu Leu Leu Lys Ser Gln Ile Cys
            260                 265                 270

Asp Asn Ala Ala Leu Tyr Ala Gln Lys Tyr Asp Glu Phe Gln Arg
        275                 280                 285

Tyr Leu Pro Arg Phe Val Thr Ala Ile Trp Asn Leu Leu Val Thr Thr
    290                 295                 300

Gly Gln Glu Val Lys Tyr Asp Leu Leu Val Ser Asn Ala Ile Gln Phe
305                 310                 315                 320

Leu Ala Ser Val Cys Glu Arg Pro His Tyr Lys Asn Leu Phe Glu Asp
                325                 330                 335

Gln Asn Thr Leu Thr Ser Ile Cys Glu Lys Val Ile Val Pro Asn Met
            340                 345                 350

Glu Phe Arg Ala Ala Asp Glu Glu Ala Phe Glu Asp Asn Ser Glu Glu
        355                 360                 365

Tyr Ile Arg Arg Asp Leu Glu Gly Ser Asp Ile Asp Thr Arg Arg Arg
    370                 375                 380

Ala Ala Cys Asp Leu Val Arg Gly Leu Cys Lys Phe Phe Glu Gly Pro
385                 390                 395                 400

Val Thr Gly Ile Phe Ser Gly Tyr Val Asn Ser Met Leu Gln Glu Tyr
                405                 410                 415

Ala Lys Asn Pro Ser Val Asn Trp Lys His Lys Asp Ala Ala Ile Tyr
            420                 425                 430

Leu Val Thr Ser Leu Ala Ser Lys Ala Gln Thr Gln Lys His Gly Ile
        435                 440                 445

Thr Gln Ala Asn Glu Leu Val Asn Leu Thr Glu Phe Phe Val Asn His
    450                 455                 460

Ile Leu Pro Asp Leu Lys Ser Ala Asn Val Asn Glu Phe Pro Val Leu
465                 470                 475                 480

Lys Ala Asp Gly Ile Lys Tyr Ile Met Ile Phe Arg Asn Gln Val Pro
                485                 490                 495

Lys Glu His Leu Leu Val Ser Ile Pro Leu Leu Ile Asn His Leu Gln
            500                 505                 510

Ala Gly Ser Ile Val Val His Thr Tyr Ala Ala His Ala Leu Glu Arg
        515                 520                 525

Leu Phe Thr Met Arg Gly Pro Asn Asn Ala Thr Leu Phe Thr Ala Ala
    530                 535                 540

Glu Ile Ala Pro Phe Val Glu Ile Leu Leu Thr Asn Leu Phe Lys Ala
545                 550                 555                 560

Leu Thr Leu Pro Gly Ser Ser Glu Asn Glu Tyr Ile Met Lys Ala Ile
```

```
                   565                 570                 575
Met Arg Ser Phe Ser Leu Leu Gln Glu Ala Ile Ile Pro Tyr Ile Pro
                580                 585                 590

Thr Leu Ile Thr Gln Leu Thr Gln Lys Leu Leu Ala Val Ser Lys Asn
            595                 600                 605

Pro Ser Lys Pro His Phe Asn His Tyr Met Phe Glu Ala Ile Cys Leu
        610                 615                 620

Ser Ile Arg Ile Thr Cys Lys Ala Asn Pro Ala Ala Val Val Asn Phe
625                 630                 635                 640

Glu Glu Ala Leu Phe Leu Val Phe Thr Glu Ile Leu Gln Asn Asp Val
                645                 650                 655

Gln Glu Phe Ile Pro Tyr Val Phe Gln Val Met Ser Leu Leu Leu Glu
            660                 665                 670

Thr His Lys Asn Asp Ile Pro Ser Ser Tyr Met Ala Leu Phe Pro His
        675                 680                 685

Leu Leu Gln Pro Val Leu Trp Glu Arg Thr Gly Asn Ile Pro Ala Leu
    690                 695                 700

Val Arg Leu Leu Gln Ala Phe Leu Glu Arg Gly Ser Asn Thr Ile Ala
705                 710                 715                 720

Ser Ala Ala Ala Asp Lys Ile Pro Gly Leu Leu Gly Val Phe Gln Lys
                725                 730                 735

Leu Ile Ala Ser Lys Ala Asn Asp His Gln Gly Phe Tyr Leu Leu Asn
            740                 745                 750

Ser Ile Ile Glu His Met Pro Pro Glu Ser Val Asp Gln Tyr Arg Lys
        755                 760                 765

Gln Ile Phe Ile Leu Leu Phe Gln Arg Leu Gln Asn Ser Lys Thr Thr
    770                 775                 780

Lys Phe Ile Lys Ser Phe Leu Val Phe Ile Asn Leu Tyr Cys Ile Lys
785                 790                 795                 800

Tyr Gly Ala Leu Ala Leu Gln Glu Ile Phe Asp Gly Ile Gln Pro Lys
                805                 810                 815

Met Phe Gly Met Val Leu Glu Lys Ile Ile Ile Pro Glu Ile Gln Lys
            820                 825                 830

Val Ser Gly Asn Val Glu Lys Lys Ile Cys Ala Val Gly Ile Thr Asn
        835                 840                 845

Leu Leu Thr Glu Cys Pro Pro Met Met Asp Thr Glu Tyr Thr Lys Leu
    850                 855                 860

Trp Thr Pro Leu Leu Gln Ser Leu Ile Gly Leu Phe Glu Leu Pro Glu
865                 870                 875                 880

Asp Asp Thr Ile Pro Asp Glu Glu His Phe Ile Asp Ile Glu Asp Thr
                885                 890                 895

Pro Gly Tyr Gln Thr Ala Phe Ser Gln Leu Ala Phe Ala Gly Lys Lys
            900                 905                 910

Glu His Asp Pro Val Gly Gln Met Val Asn Asn Pro Lys Ile His Leu
        915                 920                 925

Ala Gln Ser Leu His Met Leu Ser Thr Ala Cys Pro Gly Arg Val Pro
    930                 935                 940

Ser Met Val Ser Thr Ser Leu Asn Ala Glu Ala Leu Gln Tyr Leu Gln
945                 950                 955                 960

Gly Tyr Leu Gln Ala Ala Ser Val Thr Leu Leu
                965                 970
```

(2) INFORMATION FOR SEQ ID NO:3:

```
        (i) SEQUENCE CHARACTERISTICS:
            (A) LENGTH: 38 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTISENSE: NO (v) FRAGMENT TYPE:

(vi) ORIGINAL SOURCE:

(xi) SEQUENCE DESCRIPTION: SEQ ID NO:3:

CTGGTTCGGC CCACCTCTGA AGGTTCCAGA ATCGATAG                                38

(2) INFORMATION FOR SEQ ID NO:4:

(i) SEQUENCE CHARACTERISTICS:
            (A) LENGTH: 19 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTISENSE: NO (v) FRAGMENT TYPE:

(vi) ORIGINAL SOURCE:

(xi) SEQUENCE DESCRIPTION: SEQ ID NO:4:

TAATGAGGTC TCTCACAAA                                                    19

(2) INFORMATION FOR SEQ ID NO:5:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTISENSE: NO (v) FRAGMENT TYPE:

(vi) ORIGINAL SOURCE:

(xi) SEQUENCE DESCRIPTION: SEQ ID NO:5:

GACATCCCGT CTTCCTATAT G                                                 21

(2) INFORMATION FOR SEQ ID NO:6:

(i) SEQUENCE CHARACTERISTICS:
            (A) LENGTH: 22 base pairs
            (B) TYPE: nucleic acid
            (C) STRANDEDNESS: single
            (D) TOPOLOGY: linear (ii) MOLECULE TYPE: cDNA (iii) HYPOTHETICAL: NO
```

(iv) ANTISENSE: NO (v) FRAGMENT TYPE:

(vi) ORIGINAL SOURCE:

(xi) SEQUENCE DESCRIPTION: SEQ ID NO:6:

AAGAAGCCTC ACTAGAGCAG GA                                          22

(2) INFORMATION FOR SEQ ID NO:7:

(i) SEQUENCE CHARACTERISTICS:
               (A) LENGTH: 20 base pairs
               (B) TYPE: nucleic acid
               (C) STRANDEDNESS: single
               (D) TOPOLOGY: linear (ii) MOLECULE TYPE: cDNA (iii) HYPOTHETICAL: NO (iv) ANTISENSE: NO (v) FRAGMENT TYPE:

(vi) ORIGINAL SOURCE:

(xi) SEQUENCE DESCRIPTION: SEQ ID NO:7:

TGTGAAGCCG ATCGAGTGGC                                             20

(2) INFORMATION FOR SEQ ID NO:8:

(i) SEQUENCE CHARACTERISTICS:
               (A) LENGTH: 20 base pairs
               (B) TYPE: nucleic acid
               (C) STRANDEDNESS: single
               (D) TOPOLOGY: linear (ii) MOLECULE TYPE: cDNA (iii) HYPOTHETICAL: NO (iv) ANTISENSE: NO (v) FRAGMENT TYPE:

(vi) ORIGINAL SOURCE:

(xi) SEQUENCE DESCRIPTION: SEQ ID NO:8:

TTCAGGGACA TCCTGAAAGT                                             20

(2) INFORMATION FOR SEQ ID NO:9:

(i) SEQUENCE CHARACTERISTICS:
               (A) LENGTH: 19 base pairs
               (B) TYPE: nucleic acid
               (C) STRANDEDNESS: single
               (D) TOPOLOGY: linear (ii) MOLECULE TYPE: cDNA (iii) HYPOTHETICAL: NO (iv) ANTISENSE: NO (v) FRAGMENT TYPE:

(vi) ORIGINAL SOURCE:

(xi) SEQUENCE DESCRIPTION: SEQ ID NO:9:

CCCCACTGAT GGACACTGA                                              19

(2) INFORMATION FOR SEQ ID NO:10:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTISENSE: NO (v) FRAGMENT TYPE:

(vi) ORIGINAL SOURCE:

(xi) SEQUENCE DESCRIPTION: SEQ ID NO:10:

CTCACCATTG ATGGAACCC                                        19

(2) INFORMATION FOR SEQ ID NO:11:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTISENSE: NO (v) FRAGMENT TYPE:

(vi) ORIGINAL SOURCE:

(xi) SEQUENCE DESCRIPTION: SEQ ID NO:11:

GAGATCCTAT ACATATGGAA CTCCAGCGAT G                        31

(2) INFORMATION FOR SEQ ID NO:12:

(i) SEQUENCE CHARACTERISTICES:
        (A) LENGTH: 23 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTISENSE: NO (v) FRAGMENT TYPE:

(vi) ORIGINAL SOURCE:

(xi) SEQUENCE DESCRIPTION: SEQ ID NO:12:

TATCGCTGGA ATTCTCATCC TAC                                23

(2) INFORMATION FOR SEQ ID NO:13:

(i) SEQUENCE CHARACTERISTICS:
        (A) LENGTH: 29 base pairs
        (B) TYPE: nucleic acid
        (C) STRANDEDNESS: single
        (D) TOPOLOGY: linear -continued

```
    (ii) MOLECULE TYPE: DNA (iii) HYPOTHETICAL: NO (iv) ANTISENSE: NO (v) FRAGMENT TYPE:
         (VI) ORIGINAL SOURCE (xi) SEQUENCE DESCRIPTION: SEQ ID NO:13:

CAGTTTGTCA TATGCCTCAT TATAAAATC                              29

(2) INFORMATION FOR SEQ ID NO:14:

(i) SEQUENCE CHARACTERISTICS:
         (A) LENGTH: 30 base pairs
         (B) TYPE: nucleic acid
         (C) STRANDEDNESS: single
         (D) TOPOLOGY: linear (ii) MOLECULE TYPE: DNA (iii) HYPOTHETICAL: NO (iv) ANTISENSE: NO (v) FRAGMENT TYPE:

(vi) ORIGINAL SOURCE:

(xi) SEQUENCE DESCRIPTION: SEQ ID NO:14:

GAAGCAAAGA ATTCACTTGA AAGACGTATG                             30
```